United States Patent
Fukasawa et al.

(10) Patent No.: US 7,615,347 B2
(45) Date of Patent: Nov. 10, 2009

(54) METHOD FOR TRAPPING NUCLEIC ACIDS USING DIVALENT METAL IONS

(75) Inventors: Tadashi Fukasawa, Fuji (JP); Hiroshi Kurokawa, Fuji (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 11/660,549

(22) PCT Filed: Aug. 18, 2005

(86) PCT No.: PCT/JP2005/015051

§ 371 (c)(1),
(2), (4) Date: Jul. 20, 2007

(87) PCT Pub. No.: WO2006/019127

PCT Pub. Date: Feb. 23, 2006

(65) Prior Publication Data

US 2007/0254292 A1   Nov. 1, 2007

(30) Foreign Application Priority Data

Aug. 20, 2004  (JP) .............................. 2004-240726
Aug. 20, 2004  (JP) .............................. 2004-240727

(51) Int. Cl.
*C12Q 1/68*    (2006.01)
*C12P 19/34*   (2006.01)
*G01N 15/06*   (2006.01)
*C07H 21/00*   (2006.01)
*G01N 33/53*   (2006.01)

(52) U.S. Cl. ..................... 435/6; 435/91.1; 435/7.1; 435/7.2; 422/68.1; 536/23.1; 536/24.3

(58) Field of Classification Search ............... 435/6, 435/7.1, 7.2, 91.1; 536/23.1, 24.3; 422/68.1
See application file for complete search history.

(56) References Cited

U.S. PATENT DOCUMENTS

| 6,582,922 B1 * | 6/2003 | Daimon et al. ............... 435/6 |
| 6,689,478 B2 * | 2/2004 | Laguitton ..................... 506/16 |
| 2005/0037351 A1 | 2/2005 | Kanno et al. |

FOREIGN PATENT DOCUMENTS

| EP | 0 580 305 A2 | 1/1994 |
| JP | 6-078769 A | 3/1994 |
| WO | WO-03/006650 A1 | 1/2003 |

OTHER PUBLICATIONS

Murphy et al., Biotechnol. Prog. 2003, vol. 19, No. 3, pp. 982-986.

\* cited by examiner

*Primary Examiner*—Jezia Riley
(74) *Attorney, Agent, or Firm*—Birch, Stewart, Kolasch & Birch, LLP

(57) ABSTRACT

A method for trapping nucleic acids on a surface of a solid phase substrate, which comprises the step of contacting a sample containing nucleic acids and having a pH of 12 or higher with the surface of the solid phase substrate on which divalent metal ions are immobilized, and a method for trapping nucleic acids on a surface of a solid phase substrate, which comprises the step of contacting a sample containing nucleic acids and a magnesium compound, of which pH is adjusted to be 12 or higher, with the surface of the solid phase substrate.

37 Claims, 9 Drawing Sheets
(9 of 9 Drawing Sheet(s) Filed in Color)

Concentration of MgCl$_2$

Concentration of BSA

METHOD FOR TRAPPING NUCLEIC ACIDS USING DIVALENT METAL IONS

TECHNICAL FIELD

The present invention relates to a method for trapping nucleic acids utilizing nucleic acid aggregates formed via divalent metal ions, a divalent metal ion-immobilized substrate or the like.

BACKGROUND ART

Preparation of nucleic acids from a sample containing the nucleic acids is an important technique in the fields of biotechnology, clinical diagnosis and the like. For example, in the genetic recombination techniques, it is required to isolate both a vector DNA and DNA to be cloned, and in order to conduct a genetic screening for a hereditary disease or an oncogene, it is required to extract nucleic acids from leucocyte cells and the like in blood.

Nucleic acids do not generally exist as isolated molecules, but they exist, for example, in bacteria, cells, virus particles and the like, and enclosed in cell membranes or cell walls consisting of proteins, lipids and saccharides. Further, nucleic acids themselves form complexes with histone proteins and the like. In order to extract nucleic acids existing in such a state, operations are required for disrupting cell membranes or cell walls enclosing the nucleic acids, solubilizing proteins of the complexes by denaturation or decomposition to release the nucleic acids and extracting the released nucleic acids.

As a method for preparing nucleic acids from cells, a method is commonly applied which comprising treating a sample containing cells with SDS or proteinase K for solubilization, then denaturing and removing the proteins with phenol to purify the nucleic acids (Molecular Cloning, 2nd Edition, 9.16-9.23, Cold Spring Harbor Laboratory Press, 1989). However, this method requires time and labor, and therefore, a more convenient method has been desired.

As a more convenient method for isolating nucleic acids, for example, WO99/22021 discloses a method of using silica. In this method, cells are first treated with a chaotropic reagent to lyse the cells and thereby release nucleic acids. Then, the nucleic acids are adsorbed on a nucleic acid binding carrier comprising silica or a derivative thereof, and this carrier is washed with a chaotropic reagent or an organic solvent by centrifugation. Finally, the nucleic acids are eluted with a low salt buffer. Although this method is more convenient compared with the phenol method, the method has drawbacks of still comprising many steps and requiring a centrifugal operation. Further, the method uses a chaotropic salt or ethanol that strongly inhibits enzymatic reactions such as those of PCR, which raises drawbacks of necessity of completely removing these substances thereby operations become complicated and time consuming and the like.

A method of preparing nucleic acids from peripheral blood leucocytes using a cell adsorbing fiber aggregates such as leucocyte separation filters is disclosed in Japanese Patent Publication (KOKOKU) No. 8-24583 and Japanese Patent Unexamined Publication (KOKAI) No. 8-280384. In the method disclosed in Japanese Patent Publication No. 8-24583, blood is first passed through a leucocyte separation filter to absorb leucocytes in blood on the filter, and thereby the leucocytes are separated from the other components of blood. The filter is washed by passing TE (10 mM Tris, 1 mM EDTA, pH 7.6) thorough the filter to remove proteins such as hemoglobin. The leucocytes separated and washed as described above are frozen at, for example, −80° C., together with the filter and then thawed by being left at room temperature. Then, TE-mix (TE, 10 mM NaCl, 1.5 mM $MgCl_2$, pH 7.5) was added to the filter to collect the leucocytes adsorbed on fibrous materials of the filter from the fibrous materials. However, Japanese Patent Publication No. 8-24583 describes that the operation of extracting genomic DNA from the collected leucocytes is conducted by the conventional method (phenol treatment). Specifically, the publication describes a method of adding a surfactant such as 10% sodium dodecylsulfate (SDS) and a protease (proteinase K) to the leucocytes, incubating the mixture at 65° C. for 15 hours, then adding an RNase (RNase A), incubating the mixture at 37° C. for 1 hour, then treating the resultant with a phenol reagent, and precipitating DNAs with ethanol.

Japanese Patent Unexamined Publication No. 8-280384 discloses a method of adsorbing nucleated cells and extracting nucleic acids or proteins in the nucleated cells. As the methods of extracting nucleic acids or proteins, a method of applying a cell lysis solution to superfine fiber aggregates on which the cells are bound to lyse the cells and a method of disrupting the cells are mentioned. The advantage of this method is that the adsorbed cells per se are can be disrupted or subjected to a lysis treatment without desorption of the adsorbed cells. Since the adsorbed cells are disrupted or lysed without desorption of the adsorbed cells, this method can be more conveniently performed compared with a method of desorbing adsorbed cells. However, the method of this publication also uses conventional methods without modification for purification of nucleic acids after the cell lysis, and the publication fails to disclose a novel method. Specifically, the superfine fiber aggregates adsorbing cells are first treated with purified water or a surfactant, and nucleic acids are purified from a lysis solution which passed through the superfine fiber aggregates by the usual phenol/chloroform method.

As described above, although use of a cell adsorbing fiber aggregates such as leucocyte separation filters in the methods of preparing nucleic acids from peripheral blood leucocytes has been conventionally known, those methods are those merely performing the steps of from separating leucocytes to extracting nucleic acids by using a filter, and they use available nucleic acid purification methods for the subsequent nucleic acid purification step. Therefore, the methods have drawbacks that the nucleic acid purification step becomes complicated, and thus requires a lot of time and labor.

As a more convenient method, WO00/21973 discloses a method of directly purifying nucleic acids from cells by using a filter. This method comprises the following steps: (1) a sample containing cells is first passed through a filter to allow the cells to adsorb on the filter, (2) the cells adsorbed on the filter are then lysed, (3) the lysate is filtered through a filter, (4) nucleic acids adsorbed on the filter are washed, and (5) the nucleic acids are finally eluted from the filter. The adsorbed nucleic acids are eluted by warming to a temperature of from 40 to 125° C., and the elution buffer has a pH in the range of 5 to 11, and may have a high or low salt concentration. The value $A_{260}/A_{280}$ of the purified nucleic acids is 1.8, and they can be used as a template for PCR. WO00/21973 refers to Whatman GF/D variant filters as examples of filters usable for the purpose of purification of nucleic acids, and Whatman GF/C filters as unusable examples. It is essential that filters suitable for this method do not trap the purified DNAs when the purified DNAs are passed through the filters. Further, in this method, when the cells are lysed and passed through the filter, the yield of DNAs is decreased by 80%, and therefore the method is not practically applicable. Moreover, when nucleic acids are prepared from blood by using this method, experimenters need to hemolyze erythrocytes before lysing leucocytes. In addition, such a method of adsorbing cells on a filter and then performing the purification as described above has a drawback that the filter should be chosen depending on a type of cells.

As a further convenient method overcoming these drawbacks, WO03/006650 discloses a method of using a nonwoven fabric to separate, amplify and detect nucleic acids. This method comprises the steps of first contacting a cell extract with a nonwoven fabric to adsorb nucleic acids in the cell extract on the nonwoven fabric, and then adding a solution for amplifying the nucleic acids to the nonwoven fabric to amplify the nucleic acids using the nucleic acids adsorbed on the nonwoven fabric as a template. By this method, nucleic acids can be purified on the nonwoven fabric with an extremely convenient method of contacting nucleic acids in a sample with the nonwoven fabric without using any special reagents. Further, the nucleic acids purified on the nonwoven fabric, per se, can be subjected to an amplification reaction by contacting the nucleic acids with a reaction mixture for nucleic acid synthesis, and detection of nucleic acids can be performed conveniently. However, this method has a drawback that when nucleic acids existing at comparatively low concentrations (1 to 100 pg/mL) is to be trapped, the trapping rate is significantly reduced by influence of proteins such as albumin and globulin coexisting in the sample.

Further, as an example of use of a divalent metal ion for isolating nucleic acids, for example, a method of using silica (WO99/22021) is known. In this method, cells are first lysed by a treatment with a chaotropic reagent to release nucleic acids. Then, the nucleic acids are adsorbed on a nucleic acid binding carrier comprising silica or a derivative thereof, and this carrier is washed with a chaotropic reagent or an organic solvent by centrifugation. Finally, the nucleic acids are eluted with a low salt buffer. In this method, in order to maintain immobilization of nucleic acids on the carrier at the time of the adsorption of the nucleic acids to the carrier, various kinds of salts containing magnesium are used as additives to be added to the solution.

However, this method does not use magnesium ions as a means for trapping nucleic acids in a liquid phase by immobilizing the ions on the substrate side, and does not use magnesium ions as a primary means for isolation of nucleic acids. A method of separating double-stranded nucleic acids from proteins by using a magnesium salt is disclosed in Japanese Patent Application No. 5-164841. This method uses a polymer containing an aromatic moiety substituted with hydroxyl group and having a pK less than 9 as a substrate, and a liquid phase containing nucleic acids and proteins is contacted with the polymer at pH 7 to 10 in the presence of monovalent or multivalent cations to bind proteins and single-stranded nucleic acids to the substrate and separate double-stranded nucleic acids not bound to the substrate from the liquid phase. This method does not comprise any step of denaturing the sample under a strongly alkaline condition at a pH of 12 or higher, and magnesium is not positively immobilized on the substrate as a nucleic acid trapping agent. Furthermore, in this method, magnesium ions are not bound to the substrate in the presence of nucleic acids under a strongly alkaline condition at a pH of 12 or higher.

DISCLOSURE OF THE INVENTION

Object to be Achieved by the Invention

An object of the present invention is to provide a method for more conveniently trapping and collecting nucleic acids at a higher yield compared with the conventional methods. A further object of the present invention is to provide a quick and convenient method for preparing nucleic acids usable in the conventional nucleic acid amplification techniques.

MEANS FOR ACHIEVING THE OBJECT

The inventors of the present invention conducted various researches, and as a result, found that when a magnesium compound such as magnesium chloride was added to a sample, and then pH of the sample was increased to a level around 14 by adding a base such as sodium hydroxide, efficiency for trapping nucleic acids on a nonwoven fabric was dramatically improved even when the sample contained proteins. As a result of further researches, it was surprisingly found that nucleic acids formed aggregates by a specific action of a divalent metal ion, preferably magnesium ion, under a highly alkaline condition, and apparent sizes of nucleic acids became larger due to the formation of the aggregates, resulting in increase of efficiency for trapping the nucleic acid on a filter and thus enabling trapping of nucleic acids at a high yield from a sample containing proteins.

The inventors of the present invention also surprisingly found that when sodium hydroxide was added to a sample containing nucleic acids together with proteins to prepare a sample of which pH was elevated to a level around 14, and the sample was passed thorough a nonwoven fabric on which magnesium was immobilized, efficiency for trapping the nucleic acids on the nonwoven fabric was dramatically increased. As a result of further researches of the inventors of the present invention, it was found that binding strength of nucleic acids, denatured into single-stranded nucleic acids under a highly alkaline condition, with magnesium was extremely increased, and such nucleic acids in a liquid phase were easily trapped by magnesium on a solid phase. The present invention was accomplished on the basis of these findings.

The present invention thus provides:

a method for trapping nucleic acids in a sample on a surface of a solid phase substrate, which comprises the step of adjusting pH of the sample to be 12 or higher, and either of the following steps:

the step of binding at least one kind of divalent metal ions immobilized on the surface of the solid phase substrate with the nucleic acids in the sample to trap the nucleic acids, or the step of binding at least one kind of divalent metal ions with the nucleic acids in the sample and then contacting the nucleic acids with the surface of the solid phase substrate to trap the nucleic acids, and a method for detecting a nucleic acid in a sample, which comprises the step of adjusting pH of the sample to be 12 or higher, and either of the following steps: the step of adjusting pH of the sample to be 12 or higher, and either of the following steps: the step of binding at least one kind of divalent metal ions immobilized on a surface of a solid phase substrate with nucleic acids in the sample to trap the nucleic acids, or the step of binding at least one kind of divalent metal ions with the nucleic acids in the sample and then contacting the nucleic acids with a surface of a solid phase substrate to trap the nucleic acids, and further comprises the step of amplifying a nucleic acid having a specific nucleotide sequence by using the trapped nucleic acid as a template and detecting the nucleic acid.

In these methods, at least one kind of the divalent metal ions are preferably magnesium ions.

The present invention mentioned above will be explained as for basically divided three concepts.

According to the first concept, there is provided a method for trapping nucleic acids on a surface of a solid phase substrate, which comprises the step of contacting a sample containing nucleic acids and a divalent metal compound, preferably a magnesium compound, of which pH is adjusted to be 12 or higher, with the surface of the solid phase substrate.

This method typically comprises at least the following steps:
(a) the step of adding the divalent metal compound, preferably a magnesium compound, to the sample containing nucleic acids;
(b) the step of adding a base to the sample obtained in the step (a) to adjust pH of the sample to be 12 or higher and thereby form aggregates of the nucleic acids in the sample; and
(c) the step of contacting the sample obtained in the step (b) with the surface of the solid phase substrate to trap the nucleic acids on the surface of the solid phase substrate.

According to another embodiment, the method typically comprises at least the following steps:
(a) the step of adjusting pH of the sample containing nucleic acids to be 12 or higher;
(b) the step of adding the divalent metal compound, preferably a magnesium compound, to the sample obtained in the step (a) to form aggregates of the nucleic acids in the sample; and
(c) the step of contacting the sample obtained in the step (b) with the surface of the solid phase substrate to trap the nucleic acids on the surface of the solid phase substrate.

According to another aspect, there is provided a method for detecting a nucleic acid, which comprises the step of contacting a sample containing nucleic acids and a divalent metal compound, preferably a magnesium compound, of which pH is adjusted to be 12 or higher, with a surface of a solid phase substrate, amplifying a nucleic acid having a specific nucleotide sequence by using the nucleic acids trapped on the surface of the solid phase substrate as a template, and detecting the nucleic acid.

This method typically comprises at least the following steps:
(a) the step of adding the divalent metal compound, preferably a magnesium compound, to the sample containing nucleic acids;
(b) the step of adding a base to the sample obtained in the step (a) to adjust pH of the sample to be 12 or higher, and thereby form aggregates of the nucleic acids in the sample;
(c) the step of contacting the sample obtained in the step (b) with the surface of the solid phase substrate to trap the nucleic acids on the surface of the solid phase substrate;
(d) the step of contacting a solution containing oligonucleotide probes, mononucleotide triphosphates and nucleic acid synthetic enzyme enabling amplification of the specific nucleotide sequence with the surface of the solid phase substrate obtained in the step
(c) to amplify the nucleic acid having the specific nucleotide sequence by using the nucleic acids trapped on the surface of the solid phase substrate as a template; and
(e) the step of detecting the nucleic acid having the specific nucleotide sequence amplified in the step (d).

According to another typical embodiment, the method comprises at least:
(a) the step of adjusting pH of the sample containing nucleic acids to be 12 or higher;
(b) the step of adding the divalent metal compound, preferably a magnesium compound, to the sample obtained in the step (a) to form aggregates of the nucleic acids in the sample;
(c) the step of contacting the sample obtained in the step (b) with the surface of the solid phase substrate to trap the nucleic acids on the surface of the solid phase substrate;
(d) the step of contacting a solution containing oligonucleotide probes, mononucleotide triphosphates and nucleic acid synthetic enzyme enabling amplification of the specific nucleotide sequence with the surface of the solid phase substrate obtained in the step (c) to amplify the nucleic acid having the specific nucleotide sequence by using the nucleic acids trapped on the surface of the solid phase substrate as a template; and
(e) the step of detecting the nucleic acid having the specific nucleotide sequence amplified in the step (d).

According to another embodiment, the aforementioned steps (d) and (e) can be replaced with the following steps:
(d') the step of eluting the nucleic acids from the surface of the solid phase substrate obtained in the step (c), and adding a solution containing oligonucleotide probes, mononucleotide triphosphates and nucleic acid synthetic enzyme enabling amplification of the specific nucleotide sequence to the obtained eluate to amplify the nucleic acid having the specific nucleotide sequence by using the nucleic acids in the eluate as a template; and
(e') the step of detecting the nucleic acid having the specific nucleotide sequence amplified in the step (d').

In the aforementioned elution step, heat elution, surfactant elution or EDTA elution can be preferably performed.

According to preferred embodiments of the aforementioned inventions, there are provided the aforementioned methods, wherein the aggregates of the nucleic acids are trapped on the surface of the solid phase substrate by filtration; and the aforementioned methods, wherein the solid phase substrate is a filter.

According to the second concept, there is provided a method for trapping nucleic acids on a surface of a solid phase substrate, which comprises the step of contacting a sample containing nucleic acids, a divalent metal compound and a polymer compound having affinity for divalent metal ions, of which pH is adjusted to be 12 or higher, with the surface of the solid phase substrate.

This method typically comprises at least the following steps:
(a) the step of adding at least one kind of divalent metal compound and a polymer compound having affinity for at least one kind of the divalent metal ions to the sample containing nucleic acids;
(b) the step of adjusting pH of the sample obtained in the step (a) to be 12 or higher to form aggregates of the nucleic acids in the sample with at least one kind of the divalent metal ions and the polymer compound; and
(c) the step of contacting the sample obtained in the step (b) with the surface of the solid phase substrate to trap the aggregates of the nucleic acids on the surface of the solid phase substrate.

According to another typical embodiment, the method comprises at least:
(a) the step of adjusting pH of the sample containing nucleic acids to be 12 or higher;
(b) the step of adding at least one kind of divalent metal compound and a polymer compound having affinity for at least one kind of the divalent metal ions to the sample obtained in the step (a) to form aggregates of the nucleic acids in the sample with at least one kind of the divalent metal ions and the polymer compound; and (c) the step of contacting the sample obtained in the step (b) with the surface of the solid phase substrate to trap the aggregates of the nucleic acids on the surface of the solid phase substrate.

According to another aspect, there is provided a method for detecting a nucleic acid, which comprises the step of contacting a sample containing nucleic acids, a divalent metal compound and a polymer compound having affinity for divalent metal ions, of which pH is adjusted to be 12 or higher, with a surface of a solid phase substrate, amplifying a nucleic acid having a specific nucleotide sequence by using the nucleic acids trapped on the surface of the solid phase substrate as a template, and detecting the nucleic acid.

This method typically comprises at least the following steps:

(a) the step of adding at least one kind of the divalent metal compound and the polymer compound having affinity for at least one kind of the divalent metal ions to the sample containing nucleic acids;

(b) the step of adjusting pH of the sample obtained in the step of (a) to be 12 or higher to form aggregates of the nucleic acids in the sample with at least one kind of the divalent metal ions and the polymer compound;

(c) the step of contacting the sample obtained in the step (b) with the surface of the solid phase substrate to trap the aggregates of the nucleic acids on the surface of the solid phase substrate;

(d) the step of contacting a solution containing oligonucleotide probes, mononucleotide triphosphates and nucleic acid synthetic enzyme suitable for amplification of the specific nucleotide sequence with the surface of the solid phase substrate obtained in the step (c) to amplify the nucleic acid having the specific nucleotide sequence by using the nucleic acids trapped on the surface of the solid phase substrate as a template; and (e) the step of detecting the nucleic acid having the specific nucleotide sequence amplified in the step (d).

According to another typical embodiment, the method comprises at least:

(a) the step of adjusting pH of the sample containing nucleic acids to be 12 or higher;

(b) the step of adding at least one kind of the divalent metal compound and a polymer compound having affinity for at least one kind of the divalent metal ions to the sample obtained in the step (a) to form aggregates of the nucleic acids in the sample with at least one kind of the divalent metal ions and the polymer compound;

(c) the step of contacting the sample obtained in the step (b) with the surface of the solid phase substrate to trap the aggregates of the nucleic acids on the surface of the solid phase substrate;

(d) the step of contacting a solution containing oligonucleotide probes, mononucleotide triphosphates and nucleic acid synthetic enzyme suitable for amplification of the specific nucleotide sequence with the surface of the solid phase substrate obtained in the step (c) to amplify the nucleic acid having the specific nucleotide sequence by using the nucleic acids trapped on the surface of the solid phase substrate as a template; and (e) the step of detecting the nucleic acid having the specific nucleotide sequence amplified in the step (d).

According to the third concept, there is provided a method for trapping nucleic acids on a surface of a solid phase substrate, which comprises the step of contacting a sample containing nucleic acids and having a pH of 12 or higher with the surface of the solid phase substrate on which divalent metal ions, preferably magnesium ions, are immobilized.

This method typically comprises at least the following steps:

(a) the step of immobilizing the divalent metal ions, preferably magnesium ions, on the surface of the solid phase substrate;

(b) the step of adjusting pH of the sample containing nucleic acids to be 12 or higher; and (c) the step of contacting the sample obtained in the step (b) with the surface of the solid phase substrate obtained in the step (a) to trap the nucleic acids on the surface of the solid phase substrate.

According to another aspect, there is provided a method for detecting a nucleic acid, which comprises the step of contacting a sample containing nucleic acids and having a pH of 12 or higher with a surface of a solid phase substrate on which divalent metal ions, preferably magnesium ions, are immobilized, amplifying a nucleic acid having a specific nucleotide sequence by using the nucleic acids trapped on the surface of the solid phase substrate as a template, and detecting the nucleic acid.

This method typically comprises at least the following steps:

(a) the step of immobilizing the divalent metal ions, preferably magnesium ions, on the surface of the solid phase substrate;

(b) the step of adjusting pH of the sample to be 12 or higher;

(c) the step of contacting the sample obtained in the step (b) with the surface of the solid phase substrate obtained in the step (a) to trap the nucleic acids on the surface of the solid phase substrate;

(d) the step of contacting a solution containing oligonucleotide probes, mononucleotide triphosphates and nucleic acid synthetic enzyme enabling amplification of the specific nucleotide sequence with the surface of the solid phase substrate obtained in the step (c) to amplify the nucleic acid having the specific nucleotide sequence by using the nucleic acids trapped on the surface of the solid phase substrate as a template; and (e) the step of detecting the nucleic acid having the specific nucleotide sequence amplified in the step (d).

According to another typical embodiment, the method comprises at least the following steps:

(a) the step of immobilizing the divalent metal ions, preferably magnesium ions, on the surface of the solid phase substrate;

(b) the step of adjusting pH of the sample containing nucleic acids to be 12 or higher;

(c) the step of contacting the sample obtained in the step (b) with the surface of the solid phase substrate obtained in the step (a) to trap the nucleic acids on the surface of the solid phase substrate;

(d) the step of eluting the nucleic acids from the surface of the solid phase substrate obtained in the step (c), and adding a solution containing oligonucleotide probes, mononucleotide triphosphates and nucleic acid synthetic enzyme enabling amplification of the specific nucleotide sequence to the obtained eluate to amplify the nucleic acid having the specific nucleotide sequence by using the nucleic acids in the eluate as a template; and (e) the step of detecting the nucleic acid having the specific nucleotide sequence amplified in the step (d).

In the aforementioned elution step, heat elution, surfactant elution or EDTA elution can be preferably performed.

According to preferred embodiments of the aforementioned inventions, there are provided the aforementioned methods, wherein the nucleic acids are trapped on the surface of the solid phase substrate by filtration; the aforementioned methods, wherein the solid phase substrate is a filter; the aforementioned methods, wherein the solid phase substrate comprises a polymer having residues that can immobilize a divalent metal ion, preferably magnesium ion; the aforementioned methods, wherein the residues that can immobilize a divalent metal ion, preferably magnesium ion, are carboxylic acid residues; and the aforementioned methods, wherein the solid phase substrate is a multi-layer solid phase substrate obtained by stacking solid phase substrate layers on which divalent metal ions, preferably magnesium ions, are immobilized.

From another aspect, the present invention provides a tool for trapping nucleic acids, which comprises a solid phase substrate having a surface on which divalent metal ions, preferably magnesium ions, are immobilized; and a tool for trapping nucleic acids, which comprises a solid phase substrate of which surface has residues that can immobilize a divalent metal ion, preferably magnesium ion.

The present invention also provides a kit for detecting a nucleic acid, which comprises at least one of (a) a solid phase substrate having a surface on which divalent metal ions, preferably magnesium ions, are immobilized; and (b) oligonucleotide probes, mononucleotide triphosphates and nucleic acid synthetic enzyme enabling amplification of a specific nucleotide sequence.

EFFECT OF THE INVENTION

The methods of the present invention do not require special apparatuses for trapping, concentration, separation and purification of nucleic acids, and enable convenient trap of nucleic acids, amplification and detection of the trapped nucleic acids. The nucleic acids trapped on the surface of the solid phase substrate by divalent metal ions, preferably magnesium ions, can be used per se as a template for a nucleic acid synthesis reaction, and further, because they can be easily eluted from the surface of the solid phase substrate by an action of a surfactant, heat, a chelating agent, or the like, it is also possible to obtain an eluate containing the nucleic acids and conveniently perform nucleic acid synthesis and nucleic acid detection reactions. Furthermore, the nucleic acids trapped on the surface of the solid phase substrate by formation of aggregates via divalent metal ions, preferably magnesium ions, can be used per se as a template for a nucleic acid synthesis reaction, and further, because they can be easily eluted from the surface of the solid phase substrate by an action of a surfactant, heat, a chelating agent, or the like, it is also possible to obtain an eluate containing the nucleic acids and conveniently perform nucleic acid synthesis and nucleic acid detection reactions.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Lane 1: λ DNA
Lane 2: λ DNA+0.3% BSA
Lane 3: λ DNA+1 mM $MgCl_2$
Lane 4: λ DNA+0.3% BSA+1 mM $MgCl_2$
Lane 5: λ DNA+0.3% BSA+1 mM $MgCl_2$+1 mM EDTA

Lane 1: λ DNA
Lane 2: λ DNA+0.3% BSA
Lane 3: λ DNA+1 mM $MgCl_2$
Lane 4: λ DNA+0.3% BSA+1 mM $MgCl_2$
Lane 5: λ DNA+0.3% BSA+1 mM $MgCl_2$+1 mM EDTA

Lane 1: Not immobilized, BCG genome 200 pg/physiological saline/0.2 N NaOH
Lane 2: Not immobilized, BCG genome 200 pg+0.3% HSA/physiological saline/0.2 N NaOH
Lane 3: Magnesium immobilized, BCG genome 200 pg/physiological saline/0.2 N NaOH
Lane 4: Magnesium immobilized, BCG genome 200 pg+0.3% HSA/physiological saline/0.2 N NaOH

BEST MODE OF CARRYING OUT THE INVENTION

Figure 1:
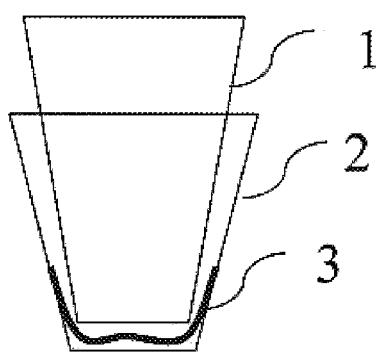
FIG. 1 shows the structure of the column used in the examples, on which a nonwoven fabric was immobilized.

In the present invention, examples of the sample containing nucleic acids include, for example, a cell extract prepared from a sample containing cells by disrupting the cells. In the specification, cells means eucaryocytes, prokaryocutes, or viruses, and include, in particular, human somatic cells, human peripheral blood leucocytes, as well as fungi, bacteria, and viruses, which may cause infectious diseases. Type of the sample is not particularly limited so long as a sample containing cells such as blood, urine, cerebrospinal fluid, sputum, body fluid, cell suspension and cell culture solution is used. Further, the sample may be a treated liquid which has been subjected to a certain treatment. Examples of the method of the treatment include a method of dissolving a highly viscous sample such as sputum with a sputum treating agent.

Cell extract means a mixture obtained by disrupting cells and containing constituents of cells. A cell extract can generally be prepared by allowing a lysis solution to act on a sample containing cells. Cell lysis solution means a solution used to disrupt cells and thereby extract nucleic acids, and contains a surfactant, an enzyme, and the like, as required. However, the solution needs not essentially contain a part or all of the above substances. As the enzyme, for example, proteases such as proteinase.K can be used, and lysozyme, lysostaphin (genus *Staphylococcus*), β-1,3-glucanase, mannase, chitinase (fungi), and the like are also used, depending on the cell species. When it is preferable to remove RNAs, an RNase such as RNase A may be added. Further, such enzymes as described above may not be contained. Animal cells can be disrupted only by contacting the cells with a hypotonic solution. Further, a cell extract can also be prepared by applying a physical force on a sample containing cells, for example, by applying supersonic waves to the sample, or disrupting the cells by using a homogenizer.

Type of the divalent metal compound is not particularly limited, so long as a substance that can supply divalent metal ions to nucleic acids in a solution is chosen. For example, a divalent metal salt or a divalent metal/polymer complex is suitable. As the divalent metal salt, for example, chlorides, sulfates, nitrates, and the like are preferred. As the divalent metal, for example, zinc, manganese, magnesium, and the like are preferred, and magnesium is most preferred. The divalent metal compound may be added to a sample such as cell lysate before pH of the sample is adjusted to a level of 12 or higher, or the compound may be added after pH of the sample is adjusted to a level of 12 or higher and before brought into contact with a surface of a solid phase substrate such as a filter. Although the concentration range of the divalent metal compound which promotes aggregation of nucleic acids is not particularly limited, the range is preferably, for example, 0.1 mM or higher.

Although the reagent for adjusting the sample to a pH of 12 or higher used in the present invention is not particularly limited, for example, a strong base such as sodium hydroxide and potassium hydroxide is preferred. By adding an appropriate volume of an aqueous solution of such a strong base, pH of the sample can be adjusted to 12 or higher.

Examples of the means for contacting a sample containing nucleic acids with a surface of a solid phase substrate include, for example, pouring a sample solution onto the surface of the solid phase substrate, penetrating a sample solution into the surface of the solid phase substrate by aspiration, pressurization or the like, immersing the solid phase substrate in a sample solution, and the like.

Although material and shape of the solid phase substrate are not particularly limited, for example, a porous sheet-shaped substrate can be used, and a filter can be preferably used. Although shape and material of the filter are not limited, examples include, for example, nonwoven fabrics, textiles, membrane filters, hollow fiber filters, sintered filters, glass fiber filters, and the like. A filter consisting of a nonwoven fabric can be preferably used as the solid phase substrate. Nonwoven fabric is a structure in the form of sheet or web prepared by adhering or confounding staples or filaments using a mechanical, thermal or chemical means (Fiber Handbook, Second edition, edited by the Society of Fiber Science and Technology, Japan, Maruzen). Although nonwoven fabrics can be produced by various methods, fundamental steps include the step of forming a web (sheet consisting of lump of fibers in the same direction to some extent), the step of adhering the web, and the finishing step. Although various fibers including natural fibers and chemical fibers are used for nonwoven fabrics, generally used are fibers of cotton, rayon, polyester, polypropylene, nylon, and the like, and as other fibers, acrylic fibers, Vinylon fibers, glass fibers, pulp, carbon fibers, and the like are also used. A nonwoven fabric consisting of polyethylene terephthalate can be preferably used. The methods for forming a web are generally classified into those of wet type, dry type and direct type. The direct type method is a method also called spinning direct-coupled type method, and includes the step of collecting fibers spun from a melted polymer solution to directly form a web. Examples of the methods classified into the direct type include the spun lace method, the spunbond method, the melt blowing method, the needle punch method, the stitch bonding method, and the like, and an ultrafine fiber nonwoven fabric produced by the melt blowing method is the most suitable for the present invention.

The means for immobilizing the divalent metal ions on the surface of the solid phase substrate is not particularly limited, and examples include, for example, a method of immobilizing divalent metal ions on a surface of a solid phase substrate having coordinate groups that form complexes with the divalent metal ions. Examples of coordinate groups that can form complexes with divalent metal generally include those of alcohol, phenol, enol, carboxylic acid, aldehyde, ketone, quinone, ether, ester, amide, nitroso compound, nitro compound, N-oxide, sulfonic acid, hypophosphorous acid, phosphorous acid, arsonic acid, primary amine, secondary amine, tertiary amine, azo compound, Schiff base, oxime, imine, enamine, and the like, and divalent metal ions can be immobilized by using one kind of these coordinate groups or a combination of two or more kinds of these coordinate groups. Examples of the solid phase substrate having these coordinate groups include organic or inorganic synthetic polymers, natural polymers, polymers obtained by chemical modification of these polymers, solid phase substrates coated with a polymer having these groups, and the like.

By amplifying a nucleic acid having a specific nucleotide sequence using the nucleic acids trapped by the surface of the solid phase substrate as a template, it can be judged whether the nucleic acid having the specific nucleotide sequence exists in a sample, and the nucleic acid having the specific nucleotide sequence contained in the sample can be thereby detected. For the amplification of nucleic acid, methods for amplifying a specific target nucleic acid sequence can be used, of which typical example is PCR. Other than PCR, methods such as ligase chain reaction (LCR), transcription-mediated amplification (TMA), branched DNA (bDNA) assay, nucleic acid sequence based amplification (NASBA), strand displacement amplification (SDA), cycling probe technology (CPT), Q-beta replicase amplification technology, rolling circle amplification technology (RCAT), loop-mediated isothermal amplification (LAMP), isothermal and chimeric primer-initiated amplification of nucleic acids (ICAN), and the like may be used. However, the nucleic acid amplification method is not limited to these examples. In Q-beta replicase amplification technology, RCAT, NASBA, SDA, TMA, LAMP, ICAN, and the like, the amplification reaction can be performed as an isothermal reaction (constant temperature), and in other methods such as PCR, LCR and the like, the amplification reaction can be performed by thermal cycling (temperature cycling).

The nucleic acid synthesis reaction used for the amplification of nucleic acid means a 5'→3' DNA or RNA synthesis reaction caused in a primer-specific manner by using a DNA-dependent DNA polymerase, a DNA-dependent RNA polymerase, an RNA-dependent RNA polymerase, a reverse transcriptase, a chain substitution type DNA polymerase, or the like. In the specification, the term "nucleic acid" is meant to an idea encompassing DNA and RNA as well as DNA and RNA containing nucleobases of non-naturally occurring types. Examples of the DNA polymerase include, but not limited to, Klenow fragment, T4 DNA polymerase, Taq DNA polymerase, and the like. Further, examples of the method for detecting a specific nucleotide sequence by a nucleic acid extension reaction using primers and a DNA polymerase include, for example, the pyrosequencing method of the aforementioned SNPs typing technology, the primer extension method, the LAMP method, and the like.

Examples of the method of detecting an amplified nucleic acid having a specific nucleotide sequence include, for example, a method of performing the detection by detecting precipitates of a reaction product of pyrophosphoric acid produced by the nucleic acid synthesis reaction and magnesium on the basis of change in transmission of light at a wavelength of 650 nm, namely, turbidity, a method of performing the detection on the basis of change in fluorescence intensity accompanying intercalation of an intercalatable fluorescent dye into nucleic acids amplified in a reaction mixture containing the dye, and the like. Examples of the intercalatable fluorescent dye include, for example, ethidium bromide, acridine orange, bisbentimide, diaminophenylindole, actinomycin, thiazole, chromomycin, derivatives thereof, and the like.

As the polymer having affinity for a divalent metal, for example, a polymer having a coordinate group which can form a complex with the divalent metal ion on a side chain can be used. Examples of the coordinate group that can form a complex with a divalent metal generally include those of alcohol, phenol, enol, carboxylic acid, aldehyde, ketone, quinone, ether, ester, amide, nitroso compound, nitro compound, N-oxide, sulfonic acid, hypophosphorous acid, phosphorous acid, arsonic acid, primary amine, secondary amine, tertiary amine, azo compound, Schiff base, oxime, imine, enamine, and the like. The polymer having affinity for a divalent metal may have two or more kinds of these coordinate groups. Examples of the polymer having these coordinate groups include organic or inorganic synthetic polymers, natural polymers, polymers obtained by chemical modification of these polymers, and the like.

Each of the aforementioned three concepts of the present invention will be explained more specifically. However, the scope of the present invention is not limited by any specific part of the following explanations.

If a nonwoven fabric (polyethylene terephthalate (PET) nonwoven fabric, A040C01, Asahi Chemical Co., Ltd.) is used for the filter as in the conventional methods, and efficiency for trapping nucleic acids on the nonwoven fabric is observed, the efficiency is extremely high when the sample consists only of a purified genomic DNA solution containing an appropriate salt, but if proteins coexist in the sample, the efficiency is drastically reduced. However, when magnesium chloride as a divalent metal compound is added to the same sample, and then pH of the sample is increased to a level of 12 or higher by adding sodium hydroxide, the efficiency for trapping nucleic acids on the nonwoven fabric is dramatically recovered. When a similar investigation was performed on the basis of reaction times of LAMP amplification reactions performed for nucleic acids trapped on the nonwoven fabric, it was revealed that the amplification reaction time of nucleic acids was markedly shortened by allowing a magnesium compound to coexist in the sample under an alkali condition, and nucleic acids serving as a template of the amplification were efficiently trapped on the filter.

One of characteristic features of the methods of the present invention is that nucleic acids can be conveniently, quickly and efficiently trapped from a sample containing proteins and the like by adding very cheap and common reagents, a divalent metal compound and an alkaline solution, without using a chaotropic salt or organic solvent such as ethanol, phenol and chloroform.

Another characteristic feature is that, after nucleic acids contained in a sample added with a divalent metal compound are trapped on a surface of a solid phase substrate under an alkali condition, a nucleic acid synthesis reaction such as PCR or following detection of a specific nucleotide sequence can be performed without eluting the nucleic acids. More specifically, processes from extraction and purification of nucleic acids to synthesis of nucleic acids, or processes from extraction and purification of nucleic acids to detection of a specific nucleobase sequence can be practiced on the same single filter. This characteristic feature markedly simplify all the steps from the extraction of nucleic acids in a sample to assay, and further, an elution operation is not required, and accordingly, treatment time can also be remarkably shortened. Further, it is also possible to conveniently perform detection for multiple targets by disposing nonwoven fabrics as the solid phase substrate in an array, or spotting nucleic acids on the same nonwoven fabric in an array.

Although a larger addition amount of the divalent metal compound is more desirable, a divalent metal ion generally forms a hydroxide under an alkali condition. For example, it is known that the solubility of magnesium hydroxide in water is extremely low, and is about 1 mM or lower. The addition amount of the divalent metal compound should be suitably determined by taking the solubility of hydroxide into consideration. For example, if the addition amount of a magnesium compound becomes 1 mM or more, clogging with a hydroxide increases aspiration resistance when a sample is aspirated using a filter as the solid phase substrate, and thus it may become difficult to trap nucleic acids on the filter. However, degree of the aspiration resistance may be adjusted by using a larger pore diameter of the filter. Therefore, the maximum addition amount of the magnesium compound is not limited to the aforementioned concentration. One of characteristics features of the present invention is that improvement of the efficiency for trapping nucleic acids on a filter can be attained by addition of a divalent metal compound at an extremely low concentration. This feature is extremely advantageous for avoiding clogging of the filter with hydroxide precipitates.

The concentration of the magnesium compound to be added is, for example, 0.01 mM or higher, preferably 0.1 mM or higher.

Further, as for the high pH condition of the sample as another characteristic of the present invention, it was demonstrated that the improving effect on the nucleic acid trapping efficiency provided by the addition of a divalent metal compound can be attained when pH is 12 or higher. For example, it is desirable to add a strong base such as sodium hydroxide to a sample to adjust pH to be about 14. Although the concentration of the base such as sodium hydroxide should be determined depending on degree of alkali resistance of the solid phase substrate such as a filter for trapping, the concentration is desirably, for example, not lower than 50 mM and not higher than 1M. By washing the filter after trapping nucleic acids with a buffer of a neutral condition, pH at the surface and inside of the filter can be lowered, and thus it becomes possible to use the trapped nucleic acids for various enzymatic reactions and the like.

Although a lot of researches have been made about interactions of a divalent metal ion and nucleic acids, there is no report of investigation about interactions of nucleic acids and metal ions under a high pH condition, because most of metal ions become hydroxides and form precipitates at a high pH. In the present invention, it has been suggested that sizes and forms of nucleic acids may change by addition of a magnesium compound in such a degree that mobility in alkaline gel electrophoresis is extremely reduced. It is considered that apparent molecular weights of nucleic acids are increased under a high pH condition due to aggregation of the nucleic acids via magnesium ions, and the trapping efficiency for nucleic acids increases when a solid phase substrate such as a filter is used as a material for filtration. The aforementioned effect is not substantially observed at a pH of 11 or lower. Although binding to phosphate groups of double-stranded nucleic acids is generally known as for interactions of nucleic acids and magnesium, the phenomenon that magnesium ions aggregate nucleic acids, under a high pH condition and at such a magnesium concentration that hydroxide precipitates is not formed, has not been reported so far. Further, there is also no report of trapping nucleic acids aggregating as described above on a solid phase substrate such as a filter.

It was also found that as for the aggregates of nucleic acids formed with divalent metal ions under a high pH condition, the aggregation was inhibited by addition of EDTA. By addition of a chelating agent such as EDTA, formation of the aggregates is easily inhibited or aggregates are destroyed, and thus the trapping efficiency is decreased. Certain kinds of samples may contain a component having a chelating ability for metal ions such as various kinds of organic acids among the components derived from living bodies. This problem can be solved by adding an excessive amount of a metal compound having a high solubility for hydroxide at a high pH. Examples of the metal of which hydroxide has a high solubility at a high pH include alkali metals and alkaline earth metals. It was revealed that, for example, when 1 mM EDTA was added to a sample containing a magnesium compound at 0.1 mM, and then a strontium compound was added at 10 mM, nucleic acids was successfully and efficiently trapped from the sample adjusted to a pH of 12 or higher.

Further, one of the characteristic features of the methods of the present invention is that the formation of the aggregates of nucleic acids formed with divalent metal ions is promoted by addition of a polymer having affinity for a divalent metal ion. For example, in a sample containing proteins at a high concentration (about 7%) such as blood serum, efficiency of the formation of aggregates of divalent metal ions and nucleic acids decreases, and decrease in the rate of trapping nucleic acids on a solid phase substrate is observed. It was revealed that when a polymer having affinity for a divalent metal ion was added to such a sample, efficiency of the formation of aggregates of divalent metal ions and nucleic acids increased, and the rate of trapping nucleic acids on a solid phase substrate was improved.

A cell extract generally contains proteins derived from living bodies in addition to nucleic acids. Although it is possible to eliminate proteins by adding proteinase K (final concentration: 0.1 mg/ml) to a sample, the treatment is not generally desirable since treatment steps of the sample increase. In the methods of the present invention, nucleic acids can be efficiently trapped on a solid phase substrate in the presence of proteins, and therefore a step of treating a sample with proteinase K before trapping of nucleic acids is usually unnecessary. However, if a filter consisting of a PET nonwoven fabric is used as the solid phase substrate for a sample containing proteins at a high concentration such as blood, clogging is highly possibly caused, and therefore it may be desirable to add proteinase K for safer aspiration. In the present invention, aggregates of nucleic acids are formed via divalent metal ions, and sizes of the aggregates become larger. Therefore, it is also possible to increase the pore diameter of the filter used for trapping nucleic acids. Accordingly, it is also possible to reduce clogging by using a filter having a larger pore diameter.

A further characteristic of the methods of the present invention is that since nucleic acids are released from cells and brought into contact with a surface of a solid phase substrate in a state of a solution, they are highly versatile methods applicable to any kind of cells. As described above, as for the cells, the methods can be used for trapping nucleic acids from eucaryocytes such as human leucocytes, prokaryocytes such as *Escherichia coli* or viruses. In a method of directly trapping cells on a solid phase substrate such as a filter and lysing the cells, characteristics of the filter or adsorption conditions should be optimized according to type of the cells. Further, since the cells should be bound to the filter while avoiding disruption of the cells, flow rate of the filtration is limited, and it is usually necessary to slowly pass the cells through the filter. When a filter is used as the solid phase substrate in the methods of the present invention, a sample such as cell extract is passed through the filter in a state of a solution, and therefore the flow rate can be increased.

Further, when a filter consisting of a nonwoven fabric is used as the solid phase substrate in the methods of the present invention, aggregates of nucleic acids formed via divalent metal ions under an alkali condition are easily trapped on the filter only by passing the sample solution thorough the filter. Number of cells contained in the sample and volume of the sample are not particularly limited, so long as they are in the ranges acceptable by the aggregate retention ability of the filter. Whilst in a method of infiltrating a cell solution such as FTA™ into a substrate and then lysing cells, the maximum sample volume that can be absorbed by a substrate serves as a maximum throughput, and therefore such a method is not so suitable for the purpose of extracting nucleic acids from a sample in a large volume. For example, when it is desired to collect nucleic acids of the total cells contained in a sample of a low cell density and large volume, it is necessary to concentrate the cells beforehand with another means such as centrifugation. When a filter is used as the solid phase substrate in the methods of the present invention, there is no such limitation concerning sample volume. Further, since a nonwoven fabric enables a treatment of a larger number of cells or a larger volume of sample per unit area, amount of immobilized nucleic acids per unit area (nucleic acid density) can be easily increased. Therefore, a filter consisting of a nonwoven fabric can be most preferably used for the methods of the present invention. Since a larger amount of nucleic acids immobilized on a filter makes detection easier, the methods of the present invention are especially useful as methods where high sensitivity is required such as in diagnosis of infectious diseases by nucleic acids amplification reactions, or as methods of tests for which nucleic acid amplification is not preferred, but a sample is comparatively easily obtained, and a larger amount of sample should be treated with a filter.

Further, unless nucleic acids in a sample are not decomposed, the methods of the present invention can be performed by using a sample stored with an arbitrary means. For example, as a sample containing cells, a sample immediately after collection or preparation may be used, or a cryopreserved sample may be used. As for blood samples, nucleic acids can be trapped and detected by using both fresh blood and cryopreserved blood.

According to another embodiment of the present invention, when a solution of magnesium chloride at a low concentration (about 0.1 mM) in 1 N sodium hydroxide is passed beforehand through a filter consisting of a nonwoven fabric, and then a nucleic acid sample containing proteins treated with sodium hydroxide is passed through the nonwoven fabric, trapping rate of the nonwoven fabric for nucleic acids is dramatically improved. Whilst, even if an aqueous magnesium chloride of the same concentration is passed through the nonwoven fabric beforehand, the nucleic acid trapping rate is not improved. In other words, this result indicates that an alkali condition is required for magnesium to adsorb on a nonwoven fabric.

A PET nonwoven fabric is generally likely to be hydrolyzed under a high pH condition, and existence ratios of carboxyl groups, hydroxyl groups, and the like increase at such hydrolyzed PET surfaces. It is estimated that divalent metal ions coordinate such functional groups having a chelating ability on the PET nonwoven fabric and are thereby immobilized on the nonwoven fabric, and therefore, in the methods of the present invention, the divalent metal ions immobilized on the solid phase play a subjective role for trapping nucleic acids in a sample liquid phase. For example, even with a nonwoven fabric obtained by hydrolyzing a filter consisting of a nonwoven fabric with a 0.125 N sodium hydroxide solution, and immersing the filter in an aqueous solution of divalent metal compound such as those of magnesium, zinc and manganese to immobilize divalent metal ions thereof on the filter, if a nucleic acids sample containing proteins and prepared at a pH of 12 or higher is passed through the nonwoven fabric, the nucleic acid trapping efficiency on the nonwoven fabric is dramatically improved. According to a further embodiment, a filter on which divalent metal ions are immobilized can also be prepared by coating a nonwoven fabric with poly-L-glutamic acid having many carboxyl groups having a chelating ability and passing an aqueous solution containing divalent metal ions through the nonwoven fabric. Further, by stacking two to four sheets of such filters to prepare a multi-layer filter, the amount of the divalent metal ions immobilized on the solid phase substrate can be increased, and thereby the nucleic acid trapping efficiency can be proportionally increased.

On the other hand, even if a nonwoven fabric on which divalent metal ions are immobilized is used, nucleic acids cannot be efficiently trapped on the nonwoven fabric from a sample not subjected to an alkaline treatment in the presence of proteins. This fact indicates that nucleic acids should be denatured under an alkali condition for binding of the divalent metal ions immobilized on the solid phase substrate to nucleic acids in a liquid phase. It was revealed by these observations that binding force between divalent metal ions and nucleic acids was remarkably increased under a high pH condition.

The methods of the present invention have a characteristic feature that nucleic acids denatured by increasing pH with an alkali are contacted with a solid phase substrate such as a nonwoven fabric on which divalent metal ions are immobilized, and this process makes it possible to achieve an extremely high trapping rate even with a sample containing proteins. Further, if nucleic acids denatured under an alkali condition are passed through a nonwoven fabric, and a LAMP amplification reaction is performed for the nucleic acids trapped on the nonwoven fabric, the nonwoven fabric on which divalent metal ions are immobilized provides an extremely shortened amplification reaction time for the nucleic acids compared with a nonwoven fabric on which divalent metal ions are not immobilized, and thus it was demonstrated that nucleic acids serving as a template of the amplification were efficiently trapped on the nonwoven fabric. Further, if the filter is washed after trapping of nucleic acids with a buffer of a neutral condition or the like to lower pH around the filter, it is also possible to use the trapped nucleic acids for various kinds of enzymatic reactions.

Further, when a filter is immersed in a nucleic acid amplification reaction solution as a solid phase substrate such as a nonwoven fabric and an amplification reaction is performed, the reaction efficiency may be decreased by a certain ratio due to adsorption of the nucleic acid amplification enzyme or the like on the filter. Such a decrease of the reaction efficiency caused by the adsorption of the nucleic acid amplification enzyme or the like on the filter can be suppressed by coating the filter, having trapped nucleic acids, beforehand with an inhibitor against enzyme adsorption. Examples of the enzyme adsorption inhibitor include bovine serum albumin, and the like.

EXAMPLES

The present invention will be explained more specifically with reference to examples. However, these examples are given for explanation, and do not limit the technical scope of the present invention.

Example 1

Comparison of LAMP Amplification Reaction Times for DNAs on Nonwoven Fabric (Magnesium Adsorption Condition)

A nonwoven fabric was cut into a disc having a diameter of 5 mm, two yellow tips (QSP Pipet Tip Yellow, 1 to 200 µL) were cut, and the nonwoven fabric was put between the tip pieces to prepare a column in which the nonwoven fabric was fixed at the tip. As the nonwoven fabric, a product of Asahi Chemical Co., Ltd., A040C01, was used (henceforth the column is referred to as "nonwoven fabric-fixed column"). The structure of the column is shown in FIG. 1. As a sample, 20 pg of *Neisseria gonorrhoeae*-derived purified genomic DNA (ATCC 700825) was dissolved in 1 mL of physiological saline or a 0.3% BSA (SIGMA-A2153) solution in physiological saline. As an alkaline treatment, 150 µL of 8 N NaOH was added to the sample to obtain a final concentration of 1 N. A 10-mL TERUMO syringe was connected to the nonwoven fabric-fixed column, and the total volume of each sample was aspirated. In the experiments (3) and (4) mentioned in FIG. 2, 1 mL of 0.1 mM solution of magnesium chloride (WAKO) in 1 N NaOH or water was passed through the nonwoven fabric-fixed column before aspiration of the sample. After the aspiration of the sample, 1 mL of TBS buffer (10 mM Tris-HCl pH 8.0, 150 mM NaCl) was further aspirated for washing.

An LAMP reaction was performed as follows. Inner primers used for the LAMP reaction mean FIP primer and BIP primer. The FIP primer is an oligonucleotide having a sequence called F1c homologous to the front strand of the target nucleic acid sequence on the 5' side and a sequence called F2 complementary to the back strand of the target nucleic acid sequence on the 3' side, and the BIP primer is an oligonucleotide having a sequence called B1c homologous to the back strand of the target nucleic acid sequence on the 5' side and a sequence called B2 complementary to the front strand of the target nucleic acid sequence on the 3' side. Outer primers mean F3 primer and B3 primer. The F3 primer is an oligonucleotide complementary to the back strand of the target nucleic acid sequence, and the B3 primer is an oligonucleotide complementary to the front strand of the target nucleic acid. Loop primers mean FL primer and BL primer, and promote the amplification reaction of nucleic acids by LAMP. The FL primer is an oligonucleotide having a sequence complementary to the sequence between the F2c sequence complementary to the F2 sequence and the F1c sequence, and the BL primer is an oligonucleotide having a sequence complementary to the sequence between the B2c sequence complementary to the B2 sequence and the B1c sequence. The methods for designing these inner primers, outer primers and loop primers are presented on the web site, http://www.eiken.co.jp/. As a target sequence of the LAMP reaction for amplifying nucleic acids, the ORF1 gene of *Neisseria gonorrhoeae* (Genebank accession No. S86113) was chosen, and amplification oligonucleotide primers for the LAMP reaction were designed. The FIP primer of SEQ ID NO: 1, the BIP primer of SEQ ID NO: 2, the F3 primer of SEQ ID NO: 3, the B3 primer of SEQ ID NO: 4, the Floop primer of SEQ ID NO: 5, and the Bloop primer of SEQ ID NO: 6 were designed, and chemically synthesized by commission to Japan Bioservice.

The materials were added to the LAMP amplification reaction mixture so that the reaction mixture contained 2.5 µM each of F3 primer and B3 primer, 20 µM each of FIP primer and BIP primer, 30 µM each of FL primer and BL primer, 1.4 mM dNTPs, 0.8 M trimethylglycine, 20 mM Tris-HCl (pH 8.8), 10 mM KCl, 10 mM $(NH_4)_2SO_4$, 0.1% Tween 20, and 6.4 units of Bst DNA polymerase large fragment (New England Biolabs), and the $MgSO_4$ concentration was 8 mM. The aforementioned LAMP amplification reaction mixture was applied in a volume of 50 µL to the washed nonwoven fabric-fixed column. The column was set in a Loopamp Reaction Tube (EIKEN CHEMICAL) so that the nonwoven fabric portion was immersed in the reaction mixture. The Loopamp Reaction Tube containing the nonwoven fabric-fixed column and the LAMP reaction mixture was lightly centrifuged in a desktop centrifugal machine (Puchi-Hachi, TOMY) for 5 seconds, and then set on a LoopAmp real-time turbidimeter LA-200 (TERAMECKS), and change of the turbidity was measured with allowing the reaction at 64° C. for 1 hour. The times until the turbidity (absorbance at 650 nm) became 0.1 were compared, which increased with generation of magnesium pyrophosphate in the LAMP amplification reaction, and is indicated in the vertical axis.

Figure 2:
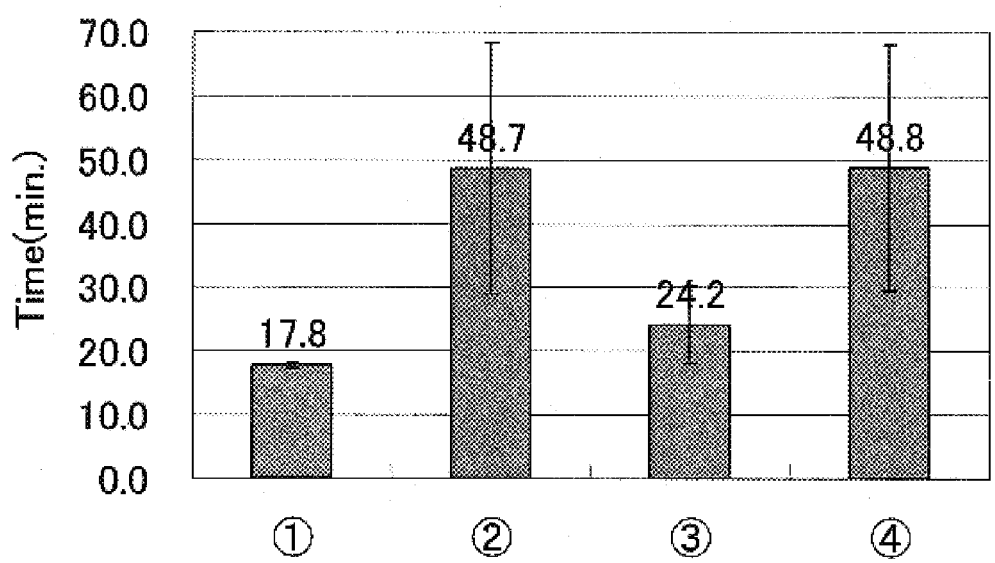
FIG. 2 shows results of comparison of the LAMP amplification reaction times of DNAs on nonwoven fabrics. The vertical axis indicates a period of time until the turbidity became 0.1.

The results are shown in FIG. 2. It can be understood that the samples containing BSA showed longer amplification times of the nucleic acids on the nonwoven fabric, that is, lower nucleic acid trapping rates. Whilst, it was found that that when the magnesium chloride solution in NaOH was aspirated beforehand, the amplification time became short to a level comparable to that shown by the samples not containing BSA, and thus the nucleic acid trapping rate was high. However, this effect was not observed with aqueous magnesium chloride. For (1) to (4) mentioned in FIG. 2, the results obtained by performing the aspiration and the measurement 3 times each (N=3) for one sample aspirated through the nonwoven fabric.

(1) *Neisseria gonorrhoeae* purified genomic DNA 20 pg/physiological saline/1 N NaOH
(2) *Neisseria gonorrhoeae* purified genomic DNA 20 pg+0.3% BSA/physiological saline/1 N NaOH
(3) 0.1 mM $MgCl_2$/*Neisseria gonorrhoeae* purified genomic DNA 20 pg+0.3% BSA after aspiration of 1 N NaOH/physiological saline/i N NaOH
(4) 0.1 mM $MgCl_2$/*Neisseria gonorrhoeae* purified genomic DNA+0.3% BSA after aspiration of physiological saline/physiological saline/1 N NaOH Example 2

Efficiency for Trapping Nucleic Acids on Magnesium-Adsorbed Nonwoven Fabric

A nonwoven fabric (A040C01) was immersed in a 0.1% aqueous solution of poly-L-glutamic acid (SIGMA, henceforth abbreviated as PLG) overnight under a room temperature condition and then dried to perform PLG coating. Cy3 fluorescence-labeled (Mirus) λ DNA (TAKARA) of 20 ng/μL was dissolved in a volume of 4 μL (80 ng) in 1 mL of a 0.3% BSA solution in physiological saline. As an alkaline treatment, 75 μL of 8 N NaOH was added to the sample to finally make it a 0.5 N NaOH solution. The labeling of DNA was performed according to the protocol attached to Mirus Label IT Cy3 Labeling Kit. A 10-mL TERUMO syringe was connected to the column on which the nonwoven fabric was fixed, and the whole volume of each sample was aspirated. The experiment was performed twice for each sample. For the experiment (2) mentioned in FIG. 3, 1 mL of 100 mM aqueous $MgCl_2$ was aspirated beforehand through the nonwoven fabric coated with 0.1% PLG before the aspiration of the sample. After all the sample was aspirated, the column was disassembled to take out the nonwoven fabric, and the nonwoven fabric was adhered to the back face of slide glass for fluorometry (MATSUNAMI) by using a mending tape. The slide glass adhered with the nonwoven fabric was set on a microarray scanner (GSI LUMONICS ScanArrayLite), a fluorescence image and fluorescence intensity were measured.

Figure 3:
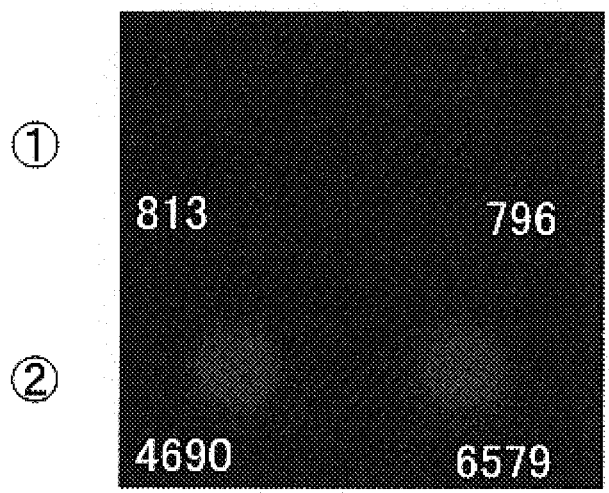
FIG. 3 shows nucleic acid trapping effect of a magnesium ion-immobilized nonwoven fabric (fluorescence intensity on the surface of the nonwoven fabric).

The results are shown in FIG. 3. Almost no trapping of nucleic acids was observed on the nonwoven fabric through which a sample containing BSA was directly passed, and thus it was demonstrated that the efficiency for trapping DNAs on the nonwoven fabric was remarkably reduced by the influence of the coexisting proteins. Whilst, it was demonstrated that, on the nonwoven fabric coated with PLG, on which magnesium was adsorbed, nucleic acids were efficiently trapped even for the sample containing BSA. The numerals mentioned in FIG. 3 represent fluorescence intensities, and (1) and (2) represent types of the nonwoven fabric. The measurement was performed for 2 spots (N=2) for each type.

Example 3

Comparison of LAMP Amplification Reaction Times for DNAs on Nonwoven Fabrics (Effect of Polymer-Coated Nonwoven Fabric and Multi-Layer Filter)

As a sample, 20 pg of *Neisseria gonorrhoeae*-derived purified genomic DNA (ATCC 700825) dissolved in 1 mL of physiological saline or a 0.3% BSA (SIGMA-A2153) solution in physiological saline was used. Coating of the nonwoven fabric with the PLG polymer was performed in the same manner as that used in Example 2. Two or four sheets of the PLG-coated nonwoven fabrics were stacked, and put between yellow chips as shown in FIG. 1 mentioned for Example 1 to prepare a multi-layer filter. As for experiments other than that for the positive control, 1 mL of 100 mM aqueous $MgCl_2$ was aspirated beforehand through the nonwoven fabric before the aspiration of the sample as in Example 2. A 10-mL TERUMO syringe was connected to the nonwoven fabric-fixed column, and the total volume of each sample was aspirated. All the preparation of the LAMP amplification reaction mixture and the turbidimetry in the amplification reaction in the nonwoven fabric-fixed column were performed in the same manner as that used in Example 1.

Figure 4:
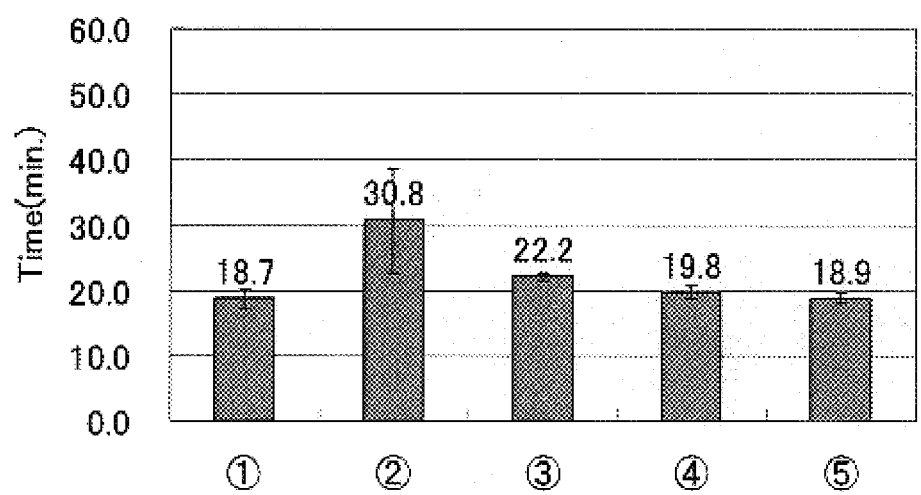
FIG. 4 shows comparison of the LAMP amplification reaction times of DNAs on nonwoven fabrics (effects of adsorption of magnesium to a polymer-coated nonwoven fabric, and a multi-layered filter). The vertical axis indicates a period of time until the turbidity became 0.1, and (1) to (5) represent different conditions of the nonwoven fabrics.

The results are shown in FIG. 4. The vertical axis indicates a period of time until the turbidity (absorbance at 650 nm) generated by production of magnesium pyrophosphate in the LAMP amplification reaction became 0.1. As for the nonwoven fabrics to which the magnesium solution was contacted, the PLG-coated one showed a higher nucleic acid trapping efficiency, and thus it was suggested that carboxyl groups were useful for adsorption of magnesium. Further, it was found that use of multiple layers for the filter increased the nucleic acid trapping rate. The aspiration and measurement were performed 3 times (N=3) for each of (1) to (5) mentioned in FIG. 4.

(1) Nonwoven fabric (one sheet, untreated), *Neisseria gonorrhoeae* purified genomic DNA 20 pg/physiological saline/1 N NaOH [positive control]
(2) Nonwoven fabric (one sheet, untreated), *Neisseria gonorrhoeae* purified genomic DNA 20 pg+0.3% BSA after aspiration of 100 mM aqueous $MgCl_2$/physiological saline/1 N NaOH
(3) Nonwoven fabric (one sheet, coated with 0.1% poly-L-glutamic acid), *Neisseria gonorrhoeae* purified genomic DNA 20 pg+0.3% BSA after aspiration of 100 mM aqueous $MgCl_2$/physiological saline/1 N NaOH
(4) Nonwoven fabric (two sheets, coated with 0.1% poly-L-glutamic acid), *Neisseria gonorrhoeae* purified genomic DNA 20 pg+0.3% BSA after aspiration of 100 mM aqueous $MgCl_2$/physiological saline/1 N NaOH
(5) Nonwoven fabric (four sheets, coated with 0.1% poly-L-glutamic acid), *Neisseria gonorrhoeae* purified genomic DNA 20 pg+0.3% BSA after aspiration of 100 mM aqueous $MgCl_2$/physiological saline/1 N NaOH Example 4

Amplification Efficiency for Nucleic Acids on Magnesium-Adsorbed Nonwoven Fabric (Influence of Presence or Absence of Alkaline Treatment of Sample)

As a sample, 20 pg of *Neisseria gonorrhoeae*-derived purified genomic DNA (ATCC 700825) dissolved in 1 mL of a 0.3% BSA (SIGMA-A2153) solution in physiological saline was used. When an alkaline treatment was used, 150 μL of 8 N NaOH was added to the sample to obtain a final concentration of 1 N. Through the nonwoven fabrics coated with PLG in the same manner as that used in Example 2, 1 mL of 100 mM aqueous $MgCl_2$ was aspirated beforehand prior to the aspiration of the sample. A 10-mL TERUMO syringe was connected to the nonwoven fabric-fixed column, and the total volume of each sample was aspirated. All the preparation of the LAMP amplification reaction mixture and the turbidimetry in the amplification reaction in the nonwoven fabric-fixed column were performed in the same manner as that used in Example 1.

Figure 5:
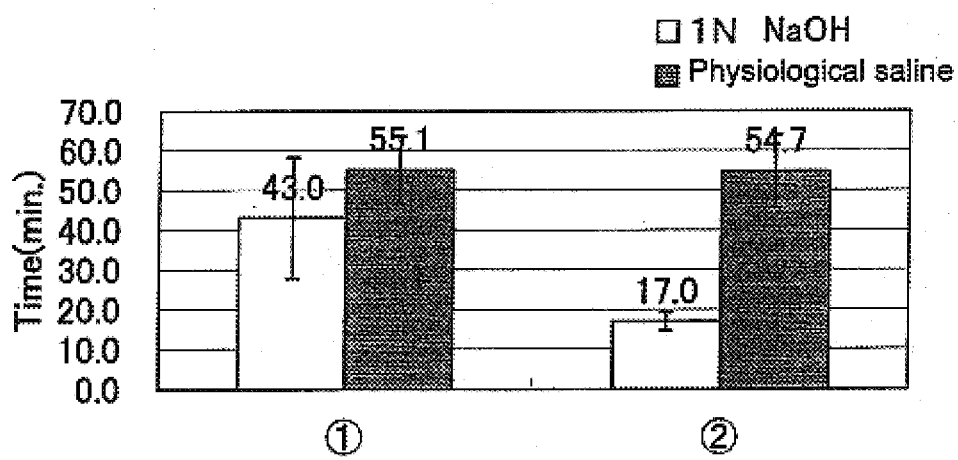
FIG. 5 shows comparison of the LAMP amplification reaction times of DNAs on nonwoven fabrics (comparison of the results obtained with or without an alkaline treatment of samples). The vertical axis indicates a period of time until the turbidity became 0.1, and (1) and (2) represent different conditions of the nonwoven fabrics.

The results are shown in FIG. 5. The vertical axis indicates a period of time until the turbidity (absorbance at 650 nm) generated by production of magnesium pyrophosphate in the LAMP amplification reaction became 0.1. It was demonstrated that, in order to trap nucleic acids from a sample containing proteins on a PLG-coated nonwoven fabric on which magnesium was adsorbed, it was necessary to subject the sample to an alkaline treatment. In FIG. 5, the left white columns represent the results obtained with physiological saline, and the right colored columns represent the results obtained with 1 N NaOH. The aspiration and measurement were performed 3 times (N=3) for each condition.

Example 5

Efficiency for Trapping Nucleic Acids of Nonwoven Fabric from Sample Containing Proteins A nonwoven fabric was cut into a disc having a diameter of 5 mm, two yellow tips (QSP Pipet Tip Yellow, 1 to 200 μL) were cut, and the nonwoven fabric was put between the tip pieces to prepare a column in which the nonwoven fabric was fixed at the tip. As the nonwoven fabric, a product of Asahi Chemical Co., Ltd., A040C01, was used (henceforth the column is referred to as "nonwoven fabric-fixed column"). The structure of the column is shown in FIG. 1. Cy3 fluorescence-labeled (Mirus) λ DNA (TAKARA) of 20 ng/μL was dissolved in a volume of 4 μL (40 ng) in 1 mL of physiological saline or a 0.3% BSA solution in physiological saline. For the negative control, 4 μL of purified water was added. The labeling of DNA was performed according to the protocol attached to Mirus Label IT Cy3 Labeling Kit. A 10-mL TERUMO syringe was connected to the column on which the nonwoven fabric was fixed, and the whole volume of each sample was aspirated. The experiment was performed twice for each sample. After the aspiration, the column was disassembled to take out the nonwoven fabric, and the nonwoven fabric was adhered to the back face of slide glass for fluorometry (MATSUNAMI) by using a mending tape. The slide glass adhered with the nonwoven fabric was set on a microarray scanner (GSI LUMONICS ScanArrayLite), and a fluorescence image and fluorescence intensity were measured.

Figure 6:
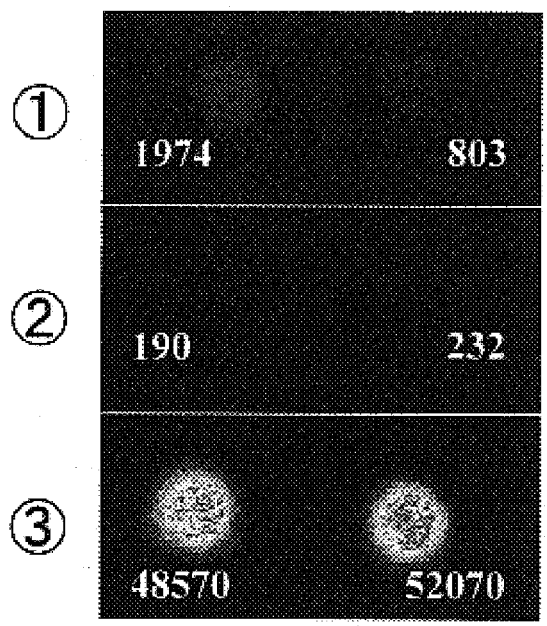
FIG. 6 shows the results of the measurement of fluorescence intensity on the surfaces of the nonwoven fabrics obtained in Example 5 (physiological saline solution samples). The numerals in the figure represent fluorescence intensities, and (1) to (3) represent the numbers of the samples aspirated through the nonwoven fabrics.

The results are shown in FIG. 6. The fluorescence intensity was markedly decreased in the sample containing 0.3% bovine serum albumin (SIGMA-A2153, henceforth abbreviated as BSA) compared with the sample not containing BSA. More specifically, it was demonstrated that the efficiency for trapping DNAs on the nonwoven fabric was remarkably reduced by the influence of the coexisting proteins. In the graph, (1) to (3) indicate the following conditions.

(1) λ DNA+0.3% BSA/physiological saline
(2) Physiological saline [negative control]
(3) λ DNA/physiological saline [positive control]

Example 6

Nucleic Acid Trapping Efficiency of Nonwoven Fabric for Magnesium/NaOH-Treated Sample The Cy3 fluorescence-labeled λ DNA of 10 ng/μL used in Example 1 was dissolved in a volume of 4 μL in 1 mL of physiological saline or a 0.3% BSA solution in physiological saline. When magnesium was added, 1 μL of 100 mM magnesium chloride (WAKO) was added to 1 mL of the sample to obtain a final concentration of 0.1 mM. Then, 75 μL of 8 N NaOH was added to the sample to finally obtain a 0.5 N NaOH solution. Each sample was aspirated through the nonwoven fabric-fixed column, and the nonwoven fabric was adhered to slide glass in the same manner as that used in Example 1. Then, the fluorescence image was measured in the same manner as that used in Example 1. The experiment was performed twice for each sample.

Figure 7:
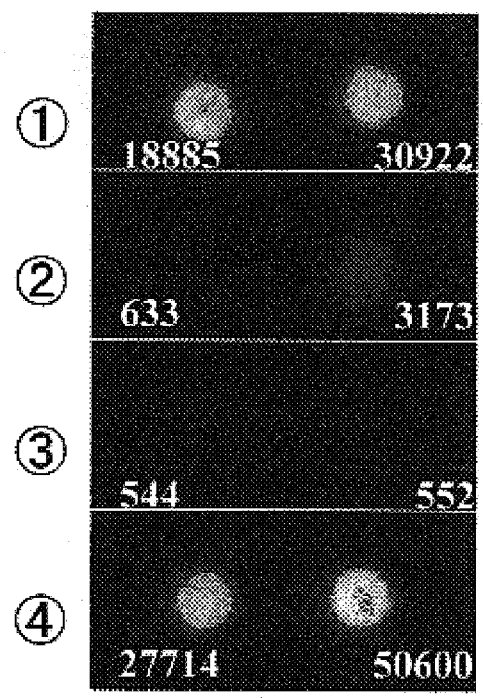
FIG. 7 shows the results of the measurement of fluorescence intensity on the surfaces of the nonwoven fabrics obtained in Example 6 (NaOH-treated samples). The numerals in the figure represent fluorescence intensities, and (1) to (4) represent the numbers of the samples aspirated through the nonwoven fabrics.

The results are shown in FIG. 7. The rate for trapping DNAs on the nonwoven fabric was remarkably decreased for the samples containing 0.3% BSA even when they are treated with NaOH. However, even among the samples containing BSA, the sample added with 0.1 mM magnesium chloride gave a trapping rate comparable to that observed for the samples not containing BSA. In the graph, (1) to (4) indicate the following conditions.

(1) λ DNA+0.3% BSA+0.1 mM $MgCl_2$/physiological saline 0.5 N NaOH
(2) λ DNA+0.3% BSA/physiological saline/0.5 N NaOH
(3) Physiological saline/0.5 N NaOH [negative control]
(4) λ DNA/physiological saline/0.5 N NaOH [positive control]

Example 7

Amplification Efficiency for Nucleic Acids Trapped on Nonwoven Fabric for Magnesium/NaOH-Treated Sample

*Neisseria gonorrhoeae*-derived purified genomic DNA (ATCC 700825) in an amount of 20 pg was dissolved in 1 mL of physiological saline or a 0.3% BSA solution in physiological saline. When magnesium was added, 1 μL of 100 mM magnesium chloride was added to 1 mL of the sample to obtain a final concentration of 0.1 mM. As an alkaline treatment, 150 μL of 8 N NaOH was added to the sample to obtain a final concentration of 1 N. The whole volume of each sample containing DNAs was aspirated through the nonwoven fabric-fixed column, and 1 mL of TBS buffer (10 mM Tris-HCl pH 8.0, 150 mM NaCl) was aspirated for washing.

An LAMP reaction was performed as follows. Inner primers used for the LAMP reaction mean FIP primer and BIP primer. The FIP primer is an oligonucleotide having a sequence called as F1c homologous to the front strand of the target nucleic acid sequence on the 5' side and a sequence called as F2 complementary to the back strand of the target nucleic acid sequence on the 3' side, and the BIP primer is an oligonucleotide having a sequence called as B1c homologous to the back strand of the target nucleic acid sequence on the 5' side and a sequence called as B2 complementary to the front strand of the target nucleic acid sequence on the 3' side. Outer primers mean F3 primer and B3 primer. The F3 primer is an oligonucleotide complementary to the back strand of the target nucleic acid sequence, and the B3 primer is an oligonucleotide complementary to the front strand of the target nucleic acid. Loop primers mean FL primer and BL primer, and promote the amplification reaction of nucleic acids by LAMP. The FL primer is an oligonucleotide having a sequence complementary to the sequence between the F2c sequence complementary to the F2 sequence and the F1c sequence, and the BL primer is an oligonucleotide having a sequence complementary to the sequence between the B2c sequence complementary to the B2 sequence and the B1c sequence. The methods for designing these inner primers, outer primers and loop primers are presented on the web site, http://www.eiken.co.jp/. As a target sequence of the LAMP reaction for amplifying nucleic acids, the ORF1 gene of *Neisseria gonorrhoeae* (Genebank accession No. S86113) was chosen, and amplification oligonucleotide primers for the LAMP reaction were designed. The FIP primer of SEQ ID NO: 1, the BIP primer of SEQ ID NO: 2, the F3 primer of SEQ ID NO: 3, the B3 primer of SEQ ID NO: 4, the Floop primer of SEQ ID NO: 5, and the Bloop primer of SEQ ID NO: 6 were designed, and chemically synthesized by commission to Japan Bioservice.

The materials were added to the LAMP amplification reaction mixture so that the reaction mixture contained 2.5 µM each of F3 primer and B3 primer, 20 µM each of FIP primer and BIP primer, 30 µM each of FL primer and BL primer, 1.4 mM dNTPs, 0.8 M trimethylglycine, 20 mM Tris-HCl (pH 8.8), 10 mM KCl, 10 mM $(NH_4)_2SO_4$, 0.1% Tween 20, and 6.4 units of Bst DNA polymerase large fragment (New England Biolabs), and the $MgSO_4$ concentration was 8 mM. The aforementioned LAMP amplification reaction mixture was applied in a volume of 50 µL to the washed nonwoven fabric-fixed column. The column was set in a Loopamp Reaction Tube (EIKEN CHEMICAL) so that the nonwoven fabric portion was immersed in the reaction mixture. The Loopamp Reaction Tube containing the nonwoven fabric-fixed column and the LAMP reaction mixture was lightly centrifuged in a desktop centrifugal machine (Puchi-Hachi, TOMY) for 5 seconds, and then set on a LoopAmp real-time turbidimeter LA-200 (TERAMECKS), and change of the turbidity was measured with allowing the reaction at 64° C. for 1 hour. The times until the turbidity (absorbance at 650 nm) became 0.1 were compared, which increased with generation of magnesium pyrophosphate in the LAMP amplification reaction, and is indicated in the vertical axis.

Figure 8:
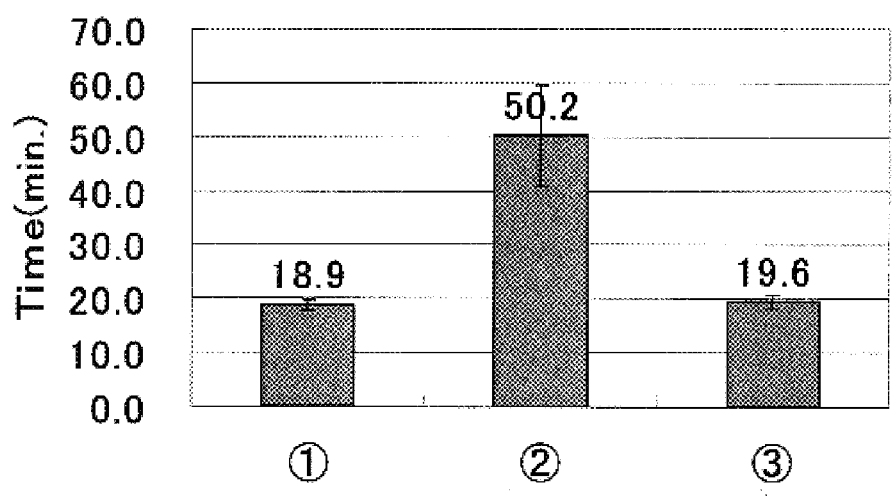
FIG. 8 shows results of comparison of the LAMP amplification reaction times of DNAs on nonwoven fabrics (confirmation of the effect of addition of magnesium chloride). The vertical axis indicates a period of time until the turbidity (absorbance at 650 nm) generated by production of magnesium pyrophosphate in the LAMP amplification reaction became 0.1, and (1) to (4) represent the numbers of the samples aspirated through the nonwoven fabrics.

The results are shown in FIG. 8. It was demonstrated that the samples containing BSA gave longer amplification times of the nucleic acids on the nonwoven fabric, i.e., lower nucleic acid trapping rates, whereas the system added with magnesium gave a short amplification time comparable to those of samples not containing BSA, i.e., a high nucleic acid trapping rate. The graph shows the results obtained by performing the aspiration and measurement 3 times (N=3) for each sample, and (1) to (3) indicate the following conditions.
(1) *Neisseria gonorrhoeae* purified genomic DNA/physiological saline/1 N NaOH
(2) *Neisseria gonorrhoeae* purified genomic DNA+0.3% BSA/physiological saline/1 N NaOH
(3) *Neisseria gonorrhoeae* purified genomic DNA+0.3% BSA+0.1 mM $MgCl_2$/physiological saline/1 N NaOH Example 8

Influence of Magnesium Concentration on Amplification Efficiency of Nucleic Acids Trapped on Nonwoven Fabric

Figure 9:
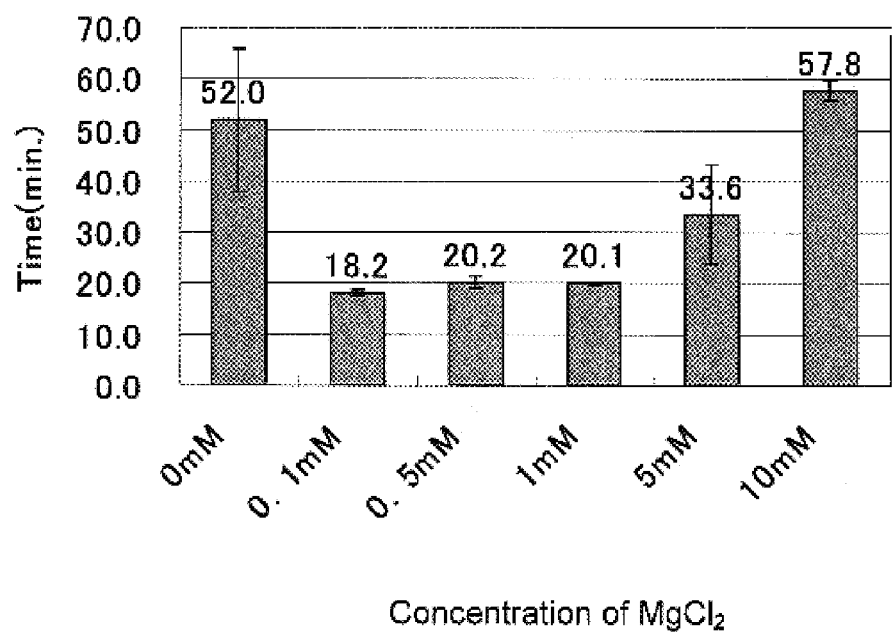
FIG. 9 shows results of comparison of the LAMP amplification reaction times of DNAs on nonwoven fabrics (test for addition concentration of magnesium chloride). The vertical axis indicates a period of time until the turbidity (absorbance at 650 nm) generated by production of magnesium pyrophosphate in the LAMP amplification reaction became 0.1.

*Neisseria gonorrhoeae* purified genomic DNA (ATCC 700825) in an amount of 20 pg was dissolved in 1 mL of a 0.3% BSA solution in physiological saline. This sample was added with 1 M $MgCl_2$ in a volume of 10 µL (final concentration: about 10 mM), or 5 µL (final concentration: about 5 mM), or 100 mM $MgCl_2$ in a volume of 10 µL (final concentration: 1 mM), 5 µL (final concentration: about 0.5 mM), or 1 µL (final concentration: about 0.1 mM). As an alkaline treatment, 150 µL of 8 N NaOH was added to the sample to obtain a final concentration of 1 N. The whole volume of each sample containing DNAs was aspirated through the nonwoven fabric-fixed column, and 1 mL of TBS buffer (10 mM Tris-HCl pH 8.0, 150 mM NaCl) was aspirated for washing. All the preparation of the LAMP amplification reaction mixture and the turbidimetry in the amplification reaction in the nonwoven fabric-fixed column were performed in the same manner as that used in Example 7. The results are shown in FIG. 9. It was demonstrated that with addition of magnesium at a concentration up to 1 mM, a high nucleic acid trapping rate was attained even in the presence of BSA.

Example 9

Influence of pH on Amplification Efficiency for Nucleic Acids Trapped on Nonwoven Fabric

Figure 10:
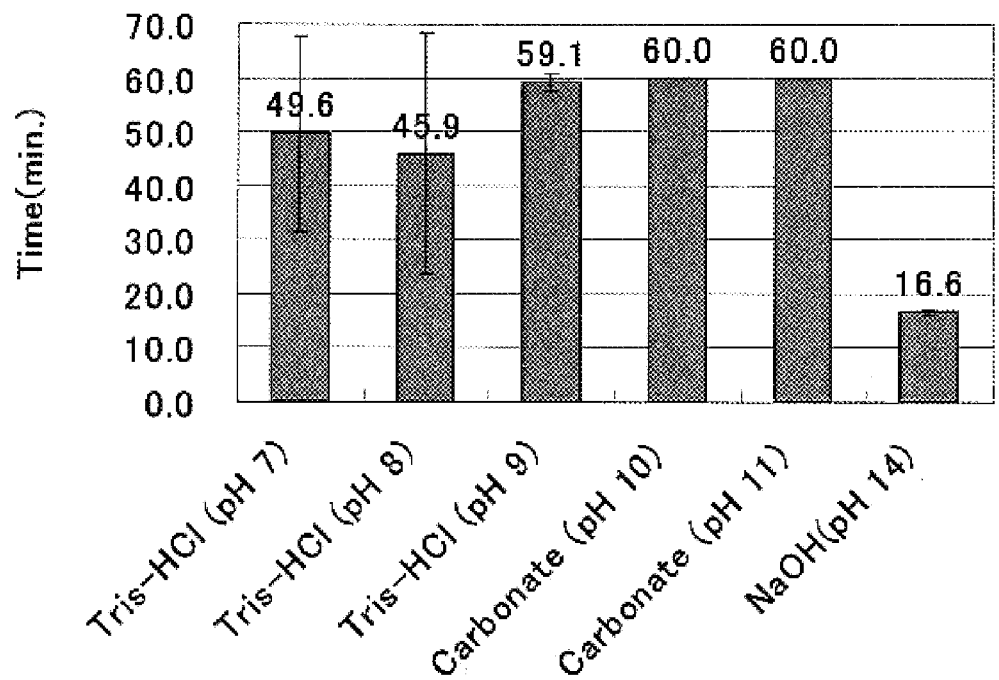
FIG. 10 shows results of comparison of the LAMP amplification reaction times of DNAs on nonwoven fabrics (test for influence of sample pH). The vertical axis indicates a period of time until the turbidity (absorbance at 650 nm) generated by production of magnesium pyrophosphate in the LAMP amplification reaction became 0.1.

*Neisseria gonorrhoeae* purified genomic DNA (ATCC 700825) in an amount of 20 pg was dissolved in 500 µL of physiological saline containing 0.6% BSA. Then, the solution was added with a 1 M buffer (Tris-HCl, pH 7.0, 8.0 or 9.0, or carbonate buffer, pH 10.0 or 11.0) or 1 N NaOH to obtain 1 mL of a sample. The whole volume of each sample containing DNAs was aspirated through the nonwoven fabric-fixed column, and 1 mL of TBS buffer (10 mM Tris-HCl pH 8.0, 150 mM NaCl) was aspirated for washing. All the preparation of the LAMP amplification reaction mixture and the turbidimetry in the amplification reaction in the nonwoven fabric-fixed column were performed in the same manner as that used in Example 7. The results are shown in FIG. 10. The results shown in the graph are results obtained by performing the aspiration and measurement 3 times (N=3) for each sample, and the vertical axis indicates a period of time until the turbidity (absorbance at 650 nm) generated by production of magnesium pyrophosphate in the LAMP amplification reaction became 0.1. For the samples having a pH around 14, i.e., samples subjected to a strong alkaline treatment, the effect of addition of magnesium was definitely demonstrated.

Example 10

Effect of Addition of Magnesium in Alkali Gel Electrophoresis

Figure 11:
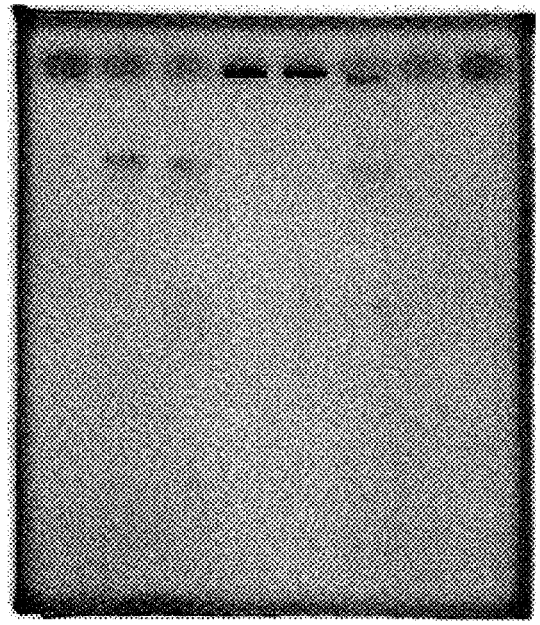
FIG. 11 shows the results of the agarose gel electrophoresis performed under an alkali condition in Example 10 (effect of addition of magnesium).

Agarose (Gibco BRL Ultra Pure) was dissolved in 0.05 N NaOH to prepare 0.5% agarose gel. To 3 µL (300 ng) of λ DNA of 100 ng/µL, 3 µL of 1% BSA was added when BSA was added, 1 µL of 10 mM $MgCl_2$ was added when $MgCl_2$ was added, 1 µL of 0.5 N NaOH was finally added to all the samples, and purified water was added to make the total volume 10 µL. To 10 µL of each sample was added 2 µL of 4× loading buffer (52% sucrose, 0.1% bromocresol green, 0.168% xylene cyanol, 200 mM NaOH), and the total volume of the sample was applied on each lane. Electrophoresis was performed at 50 V for 3 hours by immersing the gel in a 0.05 N NaOH solution as an electrophoresis buffer, and then the gel was immersed in a neutralization buffer (1 M Tris-HCl, pH 8.0, 1.5 M NaCl) for 30 minutes for neutralization. The gel was stained with ethidium bromide dissolved in the neutralization buffer for 30 minutes, and photographed by using BioImage Gel Print 20001/VGA. The results are shown in FIG. 11. Except for the samples where EDTA was added, the electrophoresis mobility of the samples containing nucleic acids and magnesium ions together was remarkably decreased. It was demonstrated by these results that aggregation of nucleic acids was caused by coexistence of nucleic acids and magnesium under an alkali condition to increase apparent sizes of nucleic acids, and the aggregation was not caused in the presence of EDTA.

Example 11

Influence of Addition Concentration of Magnesium in Alkali Gel Electrophoresis

Figure 12:
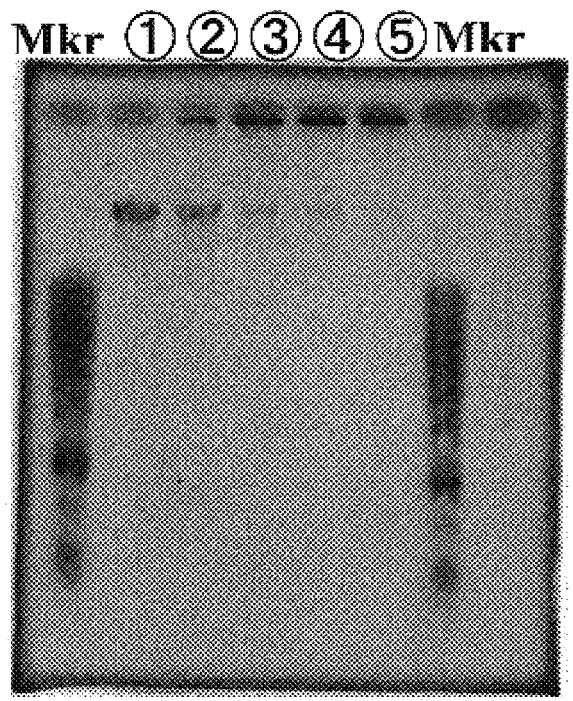
FIG. 12 shows the results of the agarose gel electrophoresis performed under an alkali condition in Example 11 (effect of addition concentration of magnesium). 5% Agarose, 0.05 N NaOH Lane 1: λ DNA+0.1 mM $MgCl_2$
Lane 2: λ DNA+0.2 mM $MgCl_2$
Lane 3: λ DNA+0.3 mM $MgCl_2$
Lane 4: λ DNA+0.4 mM $MgCl_2$
Lane 5: λ DNA+0.5 mM $MgCl_2$

The agarose gel and electrophoresis buffer used were the same as those used in Example 10. To 3 µL (300 ng) of λ DNA of 100 ng/µL was added 1 mM aqueous $MgCl_2$ in a volume of 1, 2, 3, 4 or 5 µL, and added purified water to make the total volume 10 µL. To 10 µL of each sample was added 2 µL of 4× loading buffer (52% sucrose, 0.1% bromocresol green, 0.168% xylene cyanol, 200 mM NaOH), and the total volume of the sample was applied on each lane. Electrophoresis was performed at 50 V for 3 hours by immersing the gel in a 0.05 N NaOH solution as an electrophoresis buffer, and then the gel was immersed in a neutralization buffer (1 M Tris-HCl, pH 8.0, 1.5 M NaCl) for 30 minutes for neutralization. The gel was stained with ethidium bromide dissolved in the neutralization buffer for 30 minutes, and photographed by using BioImage Gel Print 2000i/VGA. The results are shown in FIG. 12. It was demonstrated that nucleic acids having a movable size decreased with increase of the concentration of coexisting magnesium ions, and large nucleic acid components showing a low mobility increased.

Example 12

Effect of Addition of Magnesium in Gel Electrophoresis Under Condition of pH 8

Figure 13:
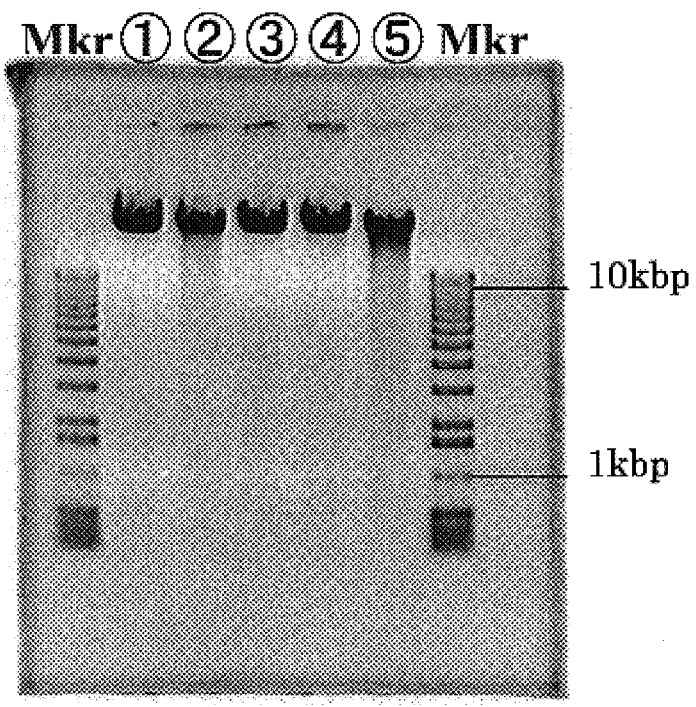
FIG. 13 shows the results of the agarose gel electrophoresis performed under a condition of pH 8 in Example 11 (effect of addition of magnesium).

Agarose (Gibco BRL Ultra Pure) was dissolved in 40 mM Tris-acetate buffer to prepare 0.5% agarose gel. To 3 µL (300 ng) of λ DNA of 100 ng/µL, 3 µL of 1% BSA was added when BSA was added, 1 µL of 10 mM $MgCl_2$ was added when $MgCl_2$ was added, and purified water was added to make the total volume 10 µL. To 10 µL of each sample was added 2 µL of 4× loading buffer (52% sucrose, 0.1% bromocresol green, 0.168% xylene cyanol), and the total volume of the sample was applied on each lane. Electrophoresis was performed at 50 V for 30 minutes by immersing the gel in 40 mM Tris-acetate buffer, and then the gel was stained with ethidium bromide, and photographed by using BioImage Gel Print 2000i/VGA. The results are shown in FIG. 13. The decrease of electrophoresis mobility caused by the interaction of nucleic acids and magnesium ions was not observed under the neutral condition, and it was demonstrated that the decrease was a phenomenon specific to an alkali condition.

Example 13

Comparison of Various Divalent Metal Ion-Immobilized Nonwoven Fabrics for Amplification Efficiency of Nucleic Acids Trapped on Nonwoven Fabrics Nonwoven fabrics cut into 3×3 cm sheets were immersed in 5 mL of a hydrolysis treatment solution consisting of a 1:1 mixture of 0.25 N NaOH and acetonitrile, and incubated at 60° C. for 1 hour with shaking. Then, the nonwoven fabrics were washed twice by immersing them in purified water for 10 minutes with shaking. The nonwoven fabrics subjected to the hydrolysis treatment were immersed in a 10 mM aqueous solution of a divalent metal chloride (zinc chloride, magnesium chloride, manganese chloride), left overnight at room temperature, then washed twice by immersing the fabrics in purified water for 10 minutes with shaking, and then dried overnight at room temperature to prepare nonwoven fabrics on which various divalent metal ions were immobilized. As a sample, 20 pg of BCG-derived purified genomic DNA was dissolved in 1 mL of physiological saline or a 0.3% human serum albumin (henceforth abbreviated as HAS, SIGMA) solution in physiological saline. To the sample was added 30 µL of 8 N NaOH to obtain a final concentration of 0.2 N. The total volume of each sample was aspirated through each of the various nonwoven fabrics, and 1 mL of TBS buffer was aspirated for washing. As for the LAMP amplification performed on the washed nonwoven fabric-fixed columns, the preparation of the LAMP amplification reaction mixture and the amplification reaction in the nonwoven fabric-fixed columns were performed in the same manner as that used in Example 7, except for the primer sets used. As for the primer sets, the sequences of 16S ribosomal RNA genes of the *Mycobacterium tuberculosis* group (GeneBank Accession No. NC_000962, X58890, X55588, AF480605) were selected as the target sequences of the LAMP reaction for amplifying nucleic acids, and amplification oligonucleotide primers for the LAMP reaction were designed. The FIP primer of SEQ ID NO: 7, the BIP primer of SEQ ID NO: 8, the F3 primer of SEQ ID NO: 9, the B3 primer of SEQ ID NO: 10, the Floop primer of SEQ ID NO: 11, and the Bloop primer of SEQ ID NO: 12 were designed, and chemically synthesized by commission to Japan Bioservice.

Figure 14:
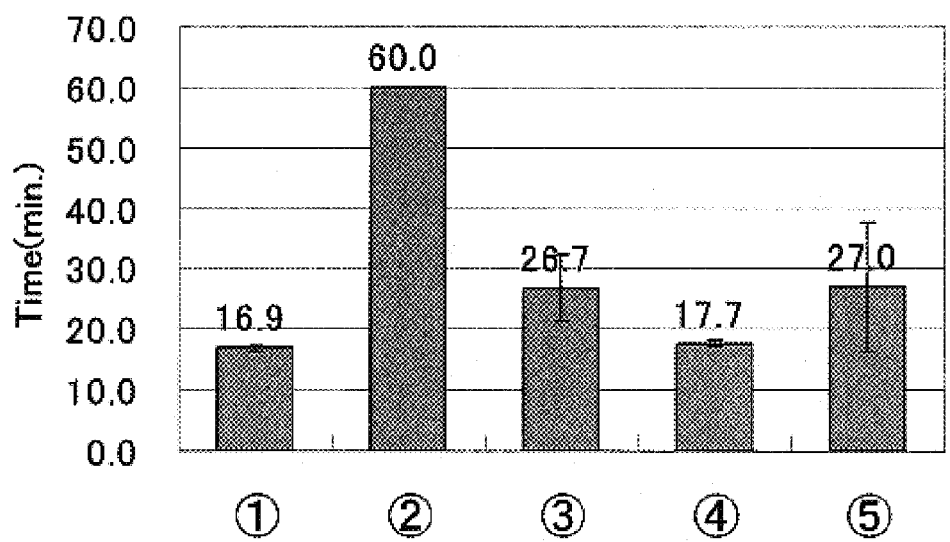
FIG. 14 shows results of comparison of the LAMP amplification reaction times of DNAs on nonwoven fabrics (comparison of nonwoven fabrics on which various divalent metal ions were immobilized). The vertical axis indicates a period of time until the turbidity (absorbance at 650 nm) generated by production of magnesium pyrophosphate in the LAMP amplification reaction became 0.1.
Figure 15:
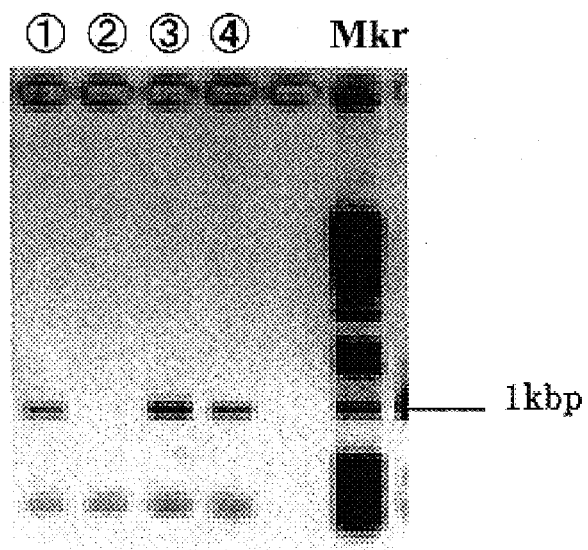
FIG. 15 shows results of agarose gel electrophoresis (1% agarose) of PCR amplification products of DNAs trapped on nonwoven fabrics. As for Lanes 1 to 4, presence or absence of magnesium ions immobilized on a nonwoven fabric used, and composition of the aspirated sample are shown in this order.
Figure 16:
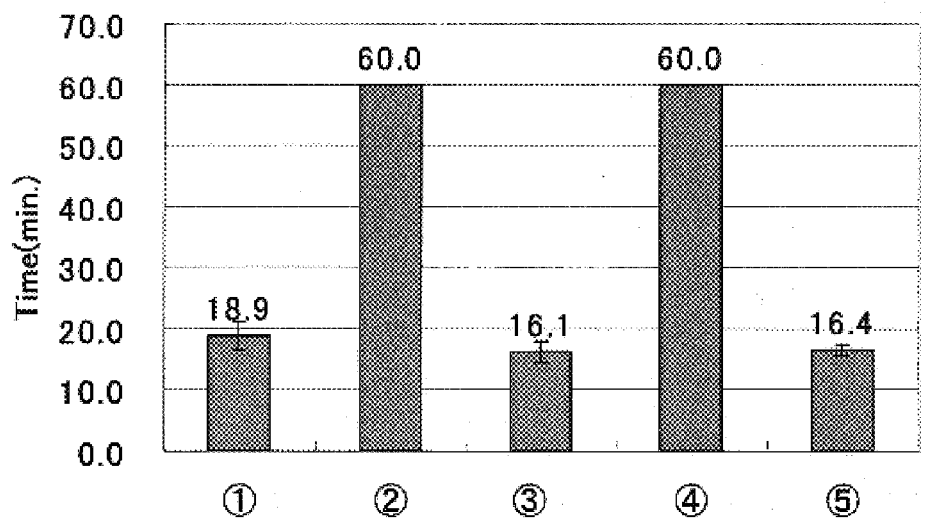
FIG. 16 shows results of comparison of the LAMP amplification reaction times of DNAs on nonwoven fabrics (effect of addition of EDTA and strontium). The vertical axis indicates a period of time until the turbidity (absorbance at 650 nm) generated by production of magnesium pyrophosphate in the LAMP amplification reaction became 0.1, and (1) to (5) represent the numbers of the samples aspirated through the nonwoven fabrics.
Figure 17:
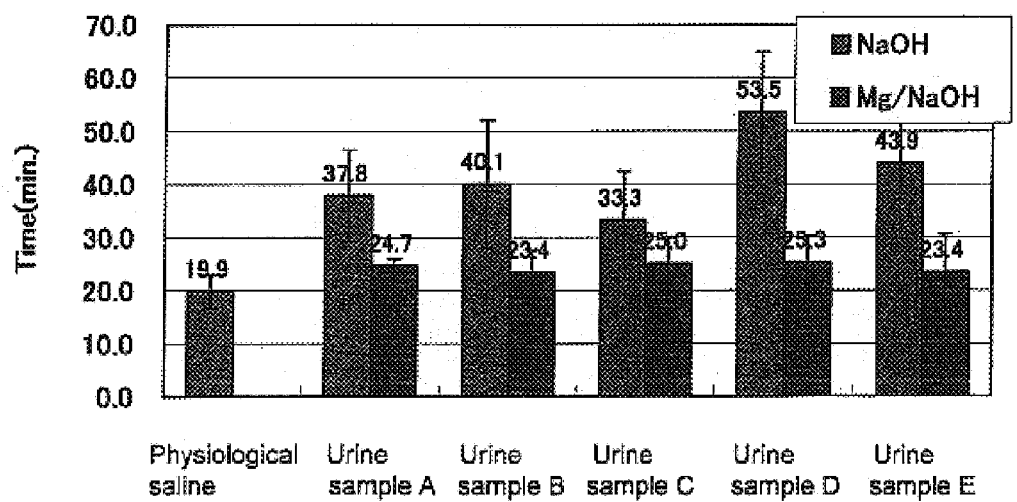
FIG. 17 shows results of comparison of the LAMP amplification reaction times of DNAs on nonwoven fabrics (nucleic acid trapping effect of magnesium-immobilized nonwoven fabric for urine sample). The vertical axis indicates a period of time until the turbidity (absorbance at 650 nm) generated by production of magnesium pyrophosphate in the LAMP amplification reaction became 0.1. The numbers below the horizontal axis represent numbers of the samples aspirated through the nonwoven fabrics. In the figure, the left bluely hatched columns indicate the results for untreated nonwoven fabrics, and the right red columns indicate the results for magnesium-immobilized nonwoven fabrics.
Figure 18:
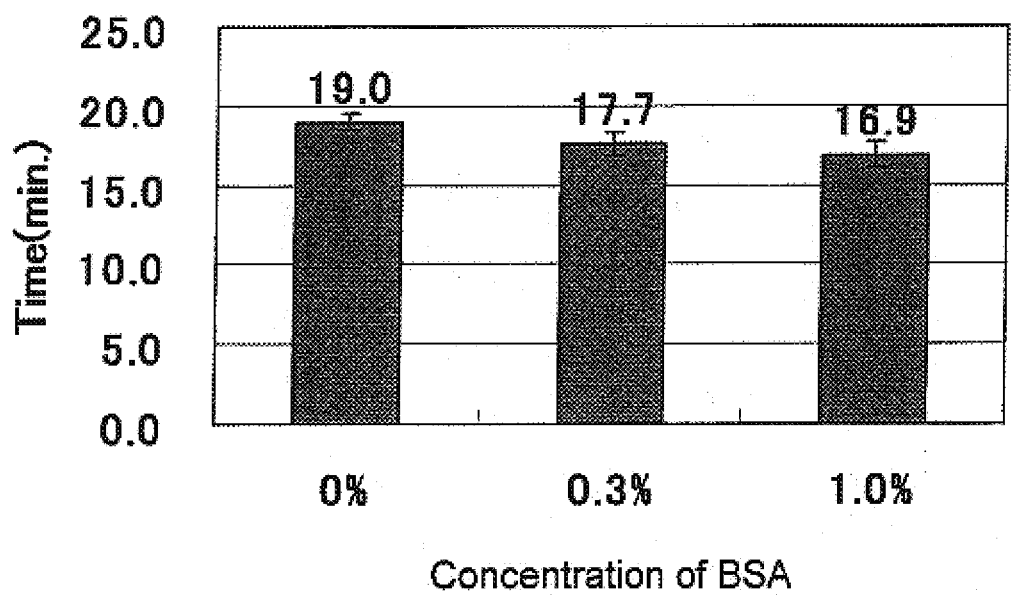
FIG. 18 shows results of comparison of the LAMP amplification reaction times of DNAs on nonwoven fabrics (effect of BSA containing washing solutions used for nonwoven fabrics after trapping of nucleic acids). The vertical axis indicates a period of time until the turbidity (absorbance at 650 nm) generated by production of magnesium pyrophosphate in the LAMP amplification reaction became 0.1. The horizontal axis indicates the concentration of BSA contained in the washing solutions.

The results are shown in FIG. 14. It was demonstrated that, other than the magnesium-immobilized nonwoven fabric, the nonwoven fabrics on which zinc or manganese was immobilized gave a high trapping rate for nucleic acids in a sample containing proteins. For (1) to (5) mentioned in the graph, the metal species immobilized on the nonwoven fabric and the aspirated sample are shown below in this order. In the graph, results obtained by performing the aspiration and measurement 3 times (N=3) for each sample are shown.
(1) Not immobilized, *Neisseria gonorrhoeae* purified genomic DNA 20 pg/physiological saline/0.2 N NaOH [Sample 1]
(2) Not immobilized, *Neisseria gonorrhoeae* purified genomic DNA 20 pg+0.3% HSA/physiological saline/0.2 N NaOH [Sample 2]
(3) Zinc, Sample 2
(4) Magnesium, Sample 2
(5) Manganese, Sample 2

Example 14

PCR Amplification Reaction of Nucleic Acids Trapped on Nonwoven Fabric

As a sample, 200 pg of BCG-derived purified genomic DNA was dissolved in 1 mL of physiological saline or a 0.3% solution of HSA (SIGMA) in physiological saline. To this sample was added 30 µL of 8 N NaOH to obtain a final concentration of 0.2 N. The whole volume of the sample containing DNAs was aspirated through untreated nonwoven fabric or the magnesium ions-immobilized nonwoven fabric, and then 1 mL of TBS buffer was aspirated for washing. The preparation method of the magnesium-immobilized nonwoven fabric was the same as that used in Example 13. As for the primer used for PCR, the sequence of 16S ribosomal RNA gene of the *Mycobacterium tuberculosis* group were selected, and the oligonucleotide primers of SEQ ID NOS: 13 and 14 designed so that the size of the amplification product should be 1 kbp were chemically synthesized by commission to Japan Bioservice. The washed nonwoven fabric-fixed column was immersed in 50 μL of a PCR mixture containing 0.2 mM dNTPs, 0.5 μM each of the aforementioned primers, and 3% Tween 20 as well as the buffer and 1.25 units of Ex Taq polymerase attached to the Ex Taq Hot Start Version (TAKARA) kit. The reaction was allowed at 95° C. for 5 minutes, then according to a cycle at 95° C. for 20 second, at 55° C. for 20 seconds and at 72° C. for 20 second, which was repeated for 30 times, and then at 72° C. for 7 minutes on a DNA Thermal Cycler (Perkin Elmer). After completion of the reaction of PCR, 1 μL of 10× loading buffer was added to 9 μL of each reaction mixture, and mixed, and the whole volume was subjected to electrophoresis on 1% agarose. The electrophoresis was performed at 100 V for 30 minutes, and then the gel was stained with ethidium bromide, and photographed by using BioImage Gel Print 20001/VGA.

The results are shown in FIG. 15. As for the nonwoven fabrics through which the samples containing HSA were aspirated, a band of the amplification product of PCR was observable on the magnesium-immobilized nonwoven fabric, whereas no amplification product was observed on the nonwoven fabric on which magnesium was not immobilized, and it was suggested that nucleic acids serving as a template in the sample were not trapped by that nonwoven fabric. It was demonstrated by the results mentioned above that nucleic acids contained in a sample containing proteins were successfully trapped with a magnesium-immobilized nonwoven fabric, and the nucleic acids trapped on the nonwoven fabric were applicable for a PCR amplification reaction.

Example 15

Amplification Efficiency for Nucleic Acids Trapped on Nonwoven Fabric from Sample Containing EDTA or Divalent Metal Ions As a sample, 20 pg of BCG-derived purified genomic DNA was dissolved in 1 mL of physiological saline or a 0.3% solution of HSA (SIGMA) in physiological saline. To this sample was added EDTA at a concentration of 1 mM when EDTA was added, strontium chloride at a concentration of 10 mM when strontium chloride was added, or magnesium chloride at a concentration of 0.1 mM when magnesium chloride was added, and 30 μL of 8 N NaOH was added to each sample to obtain a final concentration of 0.2 N. The preparation of the LAMP amplification reaction mixture and the amplification reaction in the nonwoven fabric-fixed column were performed in the same manner as that used in Example 13.

The results are shown in FIG. 16. It was demonstrated that the inhibition of aggregate formation of magnesium and nucleic acid by EDTA was suppressed by addition of strontium, and trapping of nucleic acids in a sample containing proteins was achievable even in the presence of a chelating component such as EDTA. In the graph, (1) to (5) indicates types of the samples aspirated through the nonwoven fabric as mentioned below, and the vertical axis indicates a period of time until the turbidity became 0.1. The aspiration and measurement were performed three times (N=3) for each sample.

(1) BCG purified genomic DNA 20 pg/physiological saline/0.2 N NaOH [positive control, Sample 1]
(2) BCG purified genomic DNA 20 pg+0.3% HSA/physiological saline/0.2 N NaOH (Sample 2)
(3) Sample 2+0.1 mM $MgCl_2$
(4) Sample 2+1 mM EDTA+0.1 mM $MgCl_2$
(5) Sample 2+1 mM EDTA+10 mM $SrCl_{2+0.1}$ mM $MgCl_2$ Example 16

Amplification Efficiency for Nucleic Acids Trapped on Nonwoven Fabric from Urine Sample

*Neisseria gonorrhoeae* (ATCC 700825) was cultured for 2 days on chocolate agar, and a suspension of the collected bacilli was diluted 1 million times with physiological saline. The diluted cell suspension in a volume of 10 μL was added to 500 μL of physiological saline or urine of a healthy subject. To this sample was added 75 μL of 8 N NaOH was added to obtain a final concentration of 1 N. As in Example 2, two kinds of nonwoven fabrics, untreated nonwoven fabric and magnesium-immobilized nonwoven fabric coated with PLG through which magnesium was passed, were prepared, the total volume of the urine sample was aspirated through each nonwoven fabric, and then 1 mL of TBS buffer was aspirated for washing. The preparation of the LAMP amplification reaction mixture and the amplification reaction in the nonwoven fabric-fixed column were performed in the same manner as that used in Example 7.

The results are shown in FIG. 17. It was demonstrated that the nonwoven fabric obtained by immobilizing magnesium on PLG-coated nonwoven fabric gave a clearly shorter amplification time of nucleic acids trapped on the nonwoven fabric, and thus a higher efficiency for trapping nucleic acids in a urine sample, compared with the untreated nonwoven fabric column.

Example 17

Amplification Efficiency for Nucleic Acids Trapped on Nonwoven Fabric with Use of Washing Solution Containing BSA As a sample, 20 pg of BCG-derived purified genomic DNA was dissolved in 1 mL of a 0.3% solution of HSA (SIGMA) in physiological saline. To the sample was added 30 μL of 8 N NaOH to obtain a final concentration of 0.2 N. In the same manner as that used in Example 13, a magnesium-immobilized nonwoven fabric was prepared, the total volume of the aforementioned sample was aspirated through the nonwoven fabric, and then the nonwoven fabric washed by aspiration of 1 mL of 0%, 0.3%, or 1% solution of BSA in TBS buffer. The washed nonwoven fabric-fixed column was subjected to the LAMP amplification reaction in the same manner as that used in Example 13.

The results are shown in FIG. 18. It was demonstrated that the nucleic acid amplification reaction was accelerated by coating the nonwoven fabric trapping nucleic acids with BSA, because the LAMP amplification reaction time was more shortened as the BSA content in the washing solution became higher.

Example 20

Amplification Efficiency for Nucleic Acids on Nonwoven Fabric from Sample Added with Polymer Having Affinity for Metal Ions As a sample, 100 pg of *Neisseria gonorrhoeae*-derived purified genomic DNA was dissolved in 250 μL of physiological saline or a 7% solution of HSA (SIGMA) in physiological saline. To the sample was added magnesium chloride at a concentration of 0.5 mM when magnesium chloride was added. Where a polymer having affinity for metal ions was added to the sample, 50 μL of a 20% aqueous solution of polyethylene glycol (henceforth abbreviated as PEG) having a molecular weight of 8000 (SIGMA) was added to the sample. To each sample was added 7.5 μL of 8 N NaOH to obtain a final concentration of 0.2 N. The whole volume of the aforementioned sample was aspirated through the nonwoven fabric-fixed column, and then washing was performed with 1 mL of TBS buffer. The preparation of the LAMP amplification reaction mixture and the amplification reaction in the nonwoven fabric-fixed column were performed in the same manner as that used in Example 7.

Figure 19:
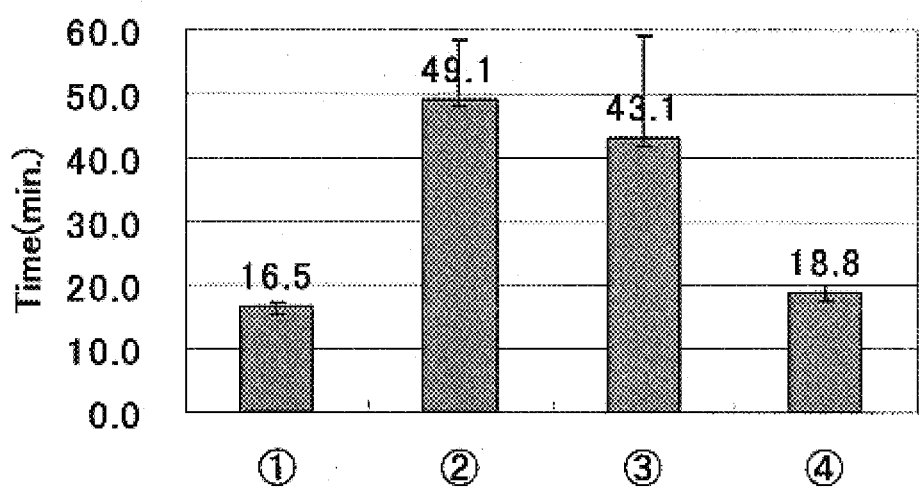
FIG. 19 shows results of comparison of the LAMP amplification reaction times of DNAs on nonwoven fabrics (effect of addition of polymer having affinity for metal ions). The vertical axis indicates a period of time until the turbidity (absorbance at 650 nm) generated by production of magnesium pyrophosphate in the LAMP amplification reaction became 0.1, and (1) to (4) represent the numbers of the samples aspirated through the nonwoven fabrics.

The results are shown in FIG. 19. At a high protein concentration of 7%, the nucleic acid trapping rate was not increased only by the addition of magnesium, and thus the LAMP amplification reaction time was long. It was suggested that use of magnesium and a polymer having affinity for metal ions in combination shortened the LAMP amplification reaction time and increased the nucleic acid trapping rate. From the above results, it was demonstrated that a polymer having affinity for metal ions promoted the action of forming aggregates of magnesium and nucleic acids.

In the graph, (1) to (4) indicates types of the aspirated samples, and the aspiration and measurement were performed 3 times (N=3) for each sample.
(1) *Neisseria gonorrhoeae* purified genomic DNA/physiological saline/0.2 N NaOH (positive control, Sample 1)
(2) *Neisseria gonorrhoeae* purified genomic DNA+7% HSA/physiological saline/0.2 N NaOH (Sample 2)
(3) Sample 2+0.5 mM $MgCl_2$
(4) Sample 2+3.3% PEG (8K)+0.5 mM $MgCl_2$

INDUSTRIAL APPLICABILITY

According to the methods of the present invention, nucleic acids can be more conveniently trapped and collected from a sample containing nucleic acids in a higher yield compared with the conventional methods. Further, the methods of the present invention can be utilized as quick and convenient nucleic acid preparation methods usable for the conventional nucleic acid amplification techniques.

The invention claimed is:

1. A method for trapping DNA in a sample on a surface of a solid phase substrate, which comprises the step of adjusting pH of the sample to be 12 or higher, and comprises either of the following steps:

the step of binding at least one kind of divalent metal ions immobilized on the surface of the solid phase substrate with the DNA in the sample to trap the DNA, or the step of binding at least one kind of divalent metal ions with the DNA in the sample and then contacting the DNA with the surface of the solid phase substrate to trap the DNA.

2. A method for detecting DNA in a sample, which comprises the step of adjusting pH of the sample to be 12 or higher, and comprises either of the following steps:

the step of binding at least one kind of divalent metal ions immobilized on a surface of a solid phase substrate with the DNA in the sample to trap the DNA, or the step of binding at least one kind of divalent metal ions with the DNA in the sample and then contacting the DNA with a surface of a solid phase substrate to trap the DNA, and further comprises the step of amplifying a nucleic acid having a specific nucleotide sequence by using the trapped DNA as a template and detecting the DNA.

3. The method according to claim 1 or 2, wherein at least one kind of the divalent metal ions are magnesium ions.

4. The method according to claim 1, which comprises at least the following steps:
   (a) the step of adding at least one kind of divalent metal compound to the sample containing DNA;
   (b) the step of adjusting pH of the sample obtained in the step (a) to be 12 or higher to form aggregates of the DNA in the sample and at least one kind of the divalent metal ions; and
   (c) the step of contacting the sample obtained in the step (b) with the surface of the solid phase substrate to trap the aggregates on the surface of the solid phase substrate.

5. The method according to claim 1, which comprises at least the following steps:
   (a) the step of adjusting pH of the sample containing DNA to be 12 or higher;
   (b) the step of adding at least one kind of divalent metal compound to the sample obtained in the step (a) to form aggregates of the DNA in the sample and at least one kind of the divalent metal ions; and
   (c) the step of contacting the sample obtained in the step (b) with the surface of the solid phase substrate to trap the aggregates on the surface of the solid phase substrate.

6. The method according to claim 2, which comprises at least the following steps:
   (a) the step of adding at least one kind of divalent metal compound to the sample containing DNA;
   (b) the step of adjusting pH of the sample obtained in the step (a) to be 12 or higher to form aggregates of the DNA in the sample and at least one kind of the divalent metal ions;
   (c) the step of contacting the sample obtained in the step (b) with the surface of the solid phase substrate to trap the aggregates on the surface of the solid phase substrate;
   (d) the step of contacting a solution containing oligonucleotide probes, mononucleotide triphosphates and nucleic acid synthetic enzyme suitable for amplification of the specific nucleotide sequence with the surface of the solid phase substrate obtained in the step (c) to amplify the nucleic acid having the specific nucleotide sequence by using the DNA trapped on the surface of the solid phase substrate as a template; and
   (e) the step of detecting the nucleic acid having the specific nucleotide sequence amplified in the step (d).

7. The method according to claim 2, which comprises at least the following steps:
   (a) the step of adjusting pH of the sample containing DNA to be 12 or higher;
   (b) the step of adding at least one kind of divalent metal compound to the sample obtained in the step (a) to form aggregates of the DNA in the sample and at least one kind of the divalent metal ions;
   (c) the step of contacting the sample obtained in the step (b) with the surface of the solid phase substrate to trap the aggregates on the surface of the solid phase substrate;
   (d) the step of contacting a solution containing oligonucleotide probes, mononucleotide triphosphates and nucleic acid synthetic enzyme suitable for amplification of the specific nucleotide sequence with the surface of the solid phase substrate obtained in the step (c) to amplify the nucleic acid having the specific nucleotide sequence by using the DNA trapped on the surface of the solid phase substrate as a template; and
   (e) the step of detecting the nucleic acid having the specific nucleotide sequence amplified in the step (d).

8. The method according to any one of claims 4 to 7, wherein the aggregates are trapped on the surface of the solid phase substrate by filtration.

9. The method according to any one of claims 4 to 7, wherein the solid phase substrate is a filter.

10. The method according to any one of claims 4 to 7, wherein the solid phase substrate is a filter consisting of a nonwoven fabric.

11. The method according to any one of claims 4 to 7, wherein at least one kind of divalent metal is magnesium.

12. The method according to claim 11, which comprises the step of adding metal ions having a solubility of 0.2 mM or higher at a pH of 12 or higher to the sample containing nucleic acids.

13. A kit for trapping DNA in a sample or a kit for trapping and detecting DNA in a sample, which comprises
   a regent for extracting DNA from the sample,
   a regent for adjusting pH of the sample to be 12 or higher,
   at least one kind of divalent metal compound,
   a solid phase substrate, and
   oligonucleotide probes, mononucleotide triphosphates and nucleic acid synthetic enzyme enabling amplification of a specific nucleotide sequence.

14. The method according to claim 1, which comprises at least the following steps:
   (a) the step of adding at least one kind of divalent metal compound and a polymer compound having affinity for at least one kind of the divalent metal ions to the sample containing DNA;
   (b) the step of adjusting pH of the sample obtained in the step (a) to be 12 or higher to form aggregates of the DNA in the sample with at least one kind of the divalent metal ions and the polymer compound; and
   (c) the step of contacting the sample obtained in the step (b) with the surface of the solid phase substrate to trap the aggregates on the surface of the solid phase substrate.

15. The method according to claim 1, which comprises at least the following steps:
   (a) the step of adjusting pH of the sample containing DNA to be 12 or higher;
   (b) the step of adding at least one kind of divalent metal compound and a polymer compound having affinity for at least one kind of the divalent metal ions to the sample obtained in the step (a) to form aggregates of the DNA in the sample with at least one kind of the divalent metal ions and the polymer compound; and
   (c) the step of contacting the sample obtained in the step (b) with the surface of the solid phase substrate to trap the aggregates on the surface of the solid phase substrate.

16. The method according to claim 2, which comprises at least the following steps:
   (a) the step of adding at least one kind of divalent metal compound and a polymer compound having affinity for at least one kind of the divalent metal ions to the sample containing DNA;
   (b) the step of adjusting pH of the sample obtained in the step of (a) to be 12 or higher to form aggregates of the DNA in the sample with at least one kind of the divalent metal ions and the polymer compound;
   (c) the step of contacting the sample obtained in the step (b) with the surface of the solid phase substrate to trap the aggregates on the surface of the solid phase substrate;
   (d) the step of contacting a solution containing oligonucleotide probes, mononucleotide triphosphates and nucleic acid synthetic enzyme suitable for amplification of the specific nucleotide sequence with the surface of the solid phase substrate obtained in the step (c) to amplify the nucleic acid having the specific nucleotide sequence by using the DNA trapped on the surface of the solid phase substrate as a template; and (e) the step of detecting the nucleic acid having the specific nucleotide sequence amplified in the step (d).

17. The method according to claim 2, which comprises at least the following steps:
   (a) the step of adjusting pH of the sample containing DNA to be 12 or higher;
   (b) the step of adding at least one kind of divalent metal compound and a polymer compound having affinity for at least one kind of the divalent metal ions to the sample obtained in the step (a) to form aggregates of the DNA in the sample with at least one kind of the divalent metal ions and the polymer compound;
   (c) the step of contacting the sample obtained in the step (b) with the surface of the solid phase substrate to trap the aggregates on the surface of the solid phase substrate;
   (d) the step of contacting a solution containing oligonucleotide probes, mononucleotide triphosphates and nucleic acid synthetic enzyme suitable for amplification of the specific nucleotide sequence with the surface of the solid phase substrate obtained in the step (c) to amplify the nucleic acid having the specific nucleotide sequence by using the DNA trapped on the surface of the solid phase substrate as a template; and
   (e) the step of detecting the nucleic acid having the specific nucleotide sequence amplified in the step (d).

18. The method according to any one of claims 14 to 17, wherein the aggregates are trapped on the surface of the solid phase substrate by filtration.

19. The method according to any one of claims 14 to 17, wherein the solid phase substrate is a filter.

20. The method according to any one of claims 14 to 17, wherein the solid phase substrate is a filter consisting of a nonwoven fabric.

21. The method according to any one of claims 14 to 17, wherein at least one kind of divalent metal is magnesium.

22. The method according to claim 21, which comprises the step of adding metal ions having a solubility of 0.2 mM or higher at a pH of 12 or higher to the sample containing nucleic acids.

23. A kit for trapping DNA in a sample or a kit for trapping and detecting DNA in a sample, which comprises:
   a reagent for extracting DNA from the sample,
   a reagent for adjusting pH of the sample to be 12 or higher,
   at least one kind of divalent metal compound,
   a polymer compound having affinity for at least one kind of divalent metal ion,
   a solid phase substrate
   oligonucleotide probes,
   mononucleotide triphosphates, and
   nucleic acid synthetic enzyme enabling amplification of a specific nucleotide sequence.

24. The method according to claim 1, which comprises at least the following steps:
   (a) the step of immobilizing at least one kind of the divalent metal ions on the surface of the solid phase substrate;
   (b) the step of adjusting pH of the sample containing DNA to be 12 or higher; and
   (c) the step of contacting the sample obtained in the step (b) with the surface of the solid phase substrate obtained in the step (a) to trap the DNA on the surface of the solid phase substrate.

25. The method according to claim 2, which comprises at least the following steps:
   (a) the step of immobilizing at least one kind of the divalent metal ions on the surface of the solid phase substrate;
   (b) the step of adjusting pH of the sample containing DNA to be 12 or higher;
   (c) the step of contacting the sample obtained in the step (b) with the surface of the solid phase substrate obtained in the step (a) to trap the DNA on the surface of the solid phase substrate;
   (d) the step of contacting a solution containing oligonucleotide probes, mononucleotide triphosphates and nucleic acid synthetic enzyme suitable for amplification of the specific nucleotide sequence with the surface of the solid phase substrate obtained in the step (c) to amplify the nucleic acid having the specific nucleotide sequence by using the DNA trapped on the surface of the solid phase substrate as a template; and
   (e) the step of detecting the DNA having the specific nucleotide sequence amplified in the step (d).

26. The method according to claim 24 or 25, wherein the DNA are trapped on the surface of the solid phase substrate by filtration.

27. The method according to any one of claims 24 to 25, wherein the solid phase substrate is a filter.

28. The method according to any one of claims 24 to 25, wherein the solid phase substrate is a filter consisting of a nonwoven fabric.

29. The method according to any one of claims 24 to 25, wherein the solid phase substrate comprises a polymer compound having residues that can immobilize at least one kind of the divalent metal ions.

30. The method according to claim 29, wherein the residues that can immobilize at least one kind of the divalent metal ions are carboxylic acid residues.

31. The method according to any one of claims 24 to 25, wherein the solid phase substrate is a multi-layer solid phase substrate obtained by stacking solid phase substrate layers which can immobilize at least one kind of the divalent metal ions.

32. The method according to any one of claims 24 to 25 wherein at least one kind of divalent metal is magnesium.

33. The method according to any one of claims 24 to 25, wherein the solid phase substrate is a solid phase substrate coated with a polymer compound having affinity for at least one kind of the divalent metal ions.

34. The method according to claim 32, which comprises the step of adding metal ions having a solubility of 0.2 mM or higher at a pH of 12 or higher to the sample containing nucleic acids.

35. A kit for trapping DNA in a sample or a kit for trapping and detecting DNA in a sample, which comprises:
   a reagent for extracting DNA from the sample,
   a reagent for adjusting pH of the sample to be 12 or higher,
   at least one kind of divalent metal compound,
   oligonucleotide probes,
   mononucleotide triphosphates,
   nucleic acid synthetic enzyme enabling amplification of a specific nucleotide sequence and either a solid phase substrate which can immobilize at least one kind of divalent metal ions or
   a solid phase substrate on which at least one kind of divalent metal ions are immobilized.

36. The method according to claim 2, wherein the solid phase substrate is coated with an enzyme adsorption inhibitor.

37. The method according to claim 36, wherein the enzyme adsorption inhibitor is bovine serum albumin.

* * * * *

SEQUENCE LISTING

```
<160> NUMBER OF SEQ ID NOS: 14

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 1
cgcccaaaca gtttcacaac ctattttcag gatgtggcgg                              40

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 2
cgatttctcc cattgggctc cttctacgat gacatcgc                                38

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 3
cttaattctt ctagtaacaa acc                                                23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide primer
```

```
<400> SEQUENCE: 4
gggaatagtt ggatcattcg g                                          21

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 5
ccagcttgat gaaagccc                                              18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 6
ggcttgcgaa agtttccg                                              18

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide primer
<220> FEATURE:
<223> OTHER INFORMATION: Description of Artificial Sequence: Synthetic
      oligonucleotide primer

<400> SEQUENCE: 7
cacccacgtg ttactcatgc aagtcgaacg gaaaggtct                       39

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 8
tcgggataag cctggaccac aagacatgca tcccgt                          36

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 9
ctggctcagg acgaacg                                               17

<210> SEQ ID NO 10
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      oligonucleotide primer

<400> SEQUENCE: 10
gctcatccca caccgc                                                       16

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 11
gttcgccact cgagtatctc cg                                                22

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 12
gaaactgggt ctaataccgg                                                   20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 13
ccatgctctt gatgccccgt tg                                                22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 14
tttagccttg cggccgtact cc                                                22
```